(12) United States Patent
Liu et al.

(10) Patent No.: US 8,697,648 B2
(45) Date of Patent: Apr. 15, 2014

(54) PROTEIN AGENT FOR DIABETES TREATMENT AND β CELL IMAGING

(75) Inventors: Zhi-Ren Liu, Atlanta, GA (US); Jie Yang, Atlanta, GA (US); Bing Xu, Atlanta, GA (US); Wangda Zhou, Manchester, CT (US); Shenghui Xue, Atlanta, GA (US)

(73) Assignee: Georgia State University Research Foundation, Inc., Atlanta, GA (US)

( * ) Notice: Subject to any disclaimer, the term of this patent is extended or adjusted under 35 U.S.C. 154(b) by 0 days.

(21) Appl. No.: 13/503,194

(22) PCT Filed: Oct. 20, 2010

(86) PCT No.: PCT/US2010/053361
§ 371 (c)(1),
(2), (4) Date: Jun. 1, 2012

(87) PCT Pub. No.: WO2011/050052
PCT Pub. Date: Apr. 28, 2011

(65) Prior Publication Data
US 2012/0244080 A1    Sep. 27, 2012

Related U.S. Application Data

(60) Provisional application No. 61/253,146, filed on Oct. 20, 2009.

(51) Int. Cl.
| | |
|---|---|
| *A61K 38/26* | (2006.01) |
| *A61K 38/00* | (2006.01) |
| *C07K 14/605* | (2006.01) |
| *C07K 19/00* | (2006.01) |
| *A61K 47/48* | (2006.01) |
| *A61K 49/08* | (2006.01) |

(52) U.S. Cl.
CPC .............. *A61K 38/26* (2013.01); *C07K 14/605* (2013.01); *C07K 2319/00* (2013.01); *A61K 38/00* (2013.01); *A61K 47/48215* (2013.01); *A61K 49/085* (2013.01)
USPC ............ 514/7.2; 514/11.7; 530/308; 530/300

(58) Field of Classification Search
CPC . A61K 38/00; A61K 38/26; A61K 47/48215; A61K 49/085; C07K 14/605; C07K 2319/00; C07K 2319/31
See application file for complete search history.

(56) References Cited

U.S. PATENT DOCUMENTS

| | | | |
|---|---|---|---|
| 2003/0143596 A1* | 7/2003 | Bentley et al. | .............. 435/6 |
| 2007/0161087 A1 | 7/2007 | Glaesner et al. | |
| 2009/0181912 A1 | 7/2009 | Wang et al. | |

FOREIGN PATENT DOCUMENTS

| | | | | |
|---|---|---|---|---|
| CN | 1483041 A | 3/2004 | | |
| WO | WO 2009/146099 A2 * | 12/2009 | ............. | A61K 49/14 |

OTHER PUBLICATIONS

Rudinger, Peptide Hormones, JA Parsons, Ed., 1976, pp. 1-7.*
SIGMA, 2004, pp. 1-2.*
Berendsen, A Glimpae of the Holy Grail?, Science, 1998, 282, pp. 642-643.*
Voet et al, Biochemistry, John Wiley & Sons Inc., 1995, pp. 235-241.*
Ngo et al, Computational Complexity, Protein Structure Protection, and the Levinthal Paradox, 1994, pp. 491-494.*
Bradley et al., Limits of Cooperativity in a Structurally Modular Protein: Response of the Notch Ankyrin Domain to Analogous Alanine Substitutions in Each Repeat, J. Mol. BIoL (2002) 324, 373-386.*
GLP-1(9-36) from anaspec, from http://www.anaspec.com/products/product.asp?id=53645, p. 1, accessed Jun. 6, 2013.*
The International Search Report and Written Opinion dated Jul. 11, 2011.
Mukai, et al., "GLP-A Receptor Antagonist as a Potential Probe for Pancreatic B-cell imaging," Biochem. and Biophy. Research Commun., Sep. 6, 2009, vol. 389, No. 3, pp. 523-526.
Picha, et al., "Protein Engineered Strategies for Sustained Glucagon-Like Peptide-1 Receptor Dependent Control of Glucose Homeostasis," Diabetes, vol. 57, No. 7, pp. 1926-1934, Jul. 31, 2008.
A translation of an Office Action in the related Chinese Patent Application No. 201080057626.6, dated Jul. 9, 2013.

* cited by examiner

*Primary Examiner* — Julie Ha
*Assistant Examiner* — Li Ni Komatsu
(74) *Attorney, Agent, or Firm* — Thomas|Horstemeyer, LLP

(57) ABSTRACT

The 30 amino acid peptide GLP-1 has been integrated into the stable host protein human calbindin D9k. The fusion protein binds to GLP-1R. The fusion protein agents can be useful for both diabetes treatment and GLP-1R receptor targeting MR imaging. The fusion protein comprises a first peptide that selectively binds to a site of a target cell and linked to a second peptide, where the fusion protein is more stable than the first peptide alone and may further comprise a detectable label. The first peptide of the fusion protein may be glucagon-like peptide-1 (GLP-1), glucagon-like peptide-1 (GLP-1)(7-36), or glucagon-like peptide-1 (GLP-1) (9-36), or a conservative variant thereof.

12 Claims, 17 Drawing Sheets

*Version c does not contain Sac I*

1 2 3 4 5 6 7 8 9 M 0 min    40 min    2 hrs    24 hrs

PROTEIN AGENT FOR DIABETES TREATMENT AND β CELL IMAGING

CROSS REFERENCE TO RELATED APPLICATION

This application claims priority to the PCT application entitled "Protein Agent for Diabetes Treatment and Beta Cell Imaging," having serial number PCT/US2010/053361, filed on Oct. 20, 2010. This application also claims priority to and benefit of U.S. Provisional Patent Application No. 61/253,146, filed on Oct. 20, 2009, which is incorporated herein by reference in its entirety.

SEQUENCE LISTING

The present disclosure includes a sequence listing incorporated herein by reference in its entirety.

TECHNICAL FIELD

The present disclosure is generally related to fusion proteins having increased stability and to methods of use as therapeutic agents in the treatment of diabetes and as imaging agents with enhanced contrast properties.

BACKGROUND

Diabetes Mellitus is characterized by a deficiency in insulin secretion and insulin resistance, or A deficiency in pancreatic β-cells resulting from autoimmune destruction. During the past 10 years, the diabetic population in the United States has increased 86%. It is estimated that over 23.6 million children and adults, or 7.8% of the population, had diabetes in 2008 (ADA, 2008), 90% of whom had type 2 diabetes. It is estimated that by the year 2030, the total number of diabetic people will rise to 366 million world-wide (Wild et al., (2004) *Diabetes Care* 27: 1047-1053). Although a number of treatments have been developed and have proved to be very effective (Riddle, M C (2002) *Diabetes Metab. Res. Rev.* 18 (Suppl. 3): S42-49), development of new treatment agents and strategies that provide lasting effects, have less drug side effects such as hypoglycemia and weight gain, and better drug administration routes, remain a major challenge in management of the disease.

Diabetes development and progression is often characterized by loss of pancreatic β-cells and β-cell functions (Stoffers, D A, (2004) *Horm. Metab. Res.* 36: 811-821; de Koning et al., (2008) *Trends Pharmacol. Sci.* 29: 218-227). The ability to assess the pancreatic islet and β-cell mass and functions would be greatly beneficial for diagnosis/prognosis of diabetes and understanding the pathogenesis of the diseases. Non-invasive assessment of pancreatic β-cells and their function will also enable better design of the disease treatment strategy and monitoring the effectiveness of therapies.

Very important progress has been made in imaging of pancreas (Holmberg & Ahlgren, (2008) *Diabetologia* 51: 2148-2154). However, there are several important challenges in the imaging of pancreatic islets, especially the islet β-cells. The pancreatic islets are small and distributed throughout the entire pancreas, this demanding a high resolution imaging method to clearly locate and estimate the β-cell mass in islets of the pancreas. The pancreas islet is a tissue mass of many endocrine cell types, including a-cell, β-cells, δ-cells, ε-cells, and PP cells, and these different types of cells are completely intermingled throughout the islet.

Imaging tools or agents targeting β-cell specific molecular markers are required to image β-cells in the pancreatic islets. No successful imaging method that allows non-invasive imaging of pancreatic β-cells is currently available.

Glucagon-like Peptide-1 (GLP-1), a 30 amino-acid peptide, is one of the major incretin hormonal intestinal-derived factors secreted to lower the blood glucose (Drucker, D J, (2006) *Cell Metab.* 3: 153-165). The peptide is produced in enteroendocrine L cells in small bowel and colon. GLP-1 is secreted by the L cells as a 37 amino acids precursor and the peptide is processed to a bioactive form of a 30 amino acid (7-37) amide (Baggio & Drucker (2007) *Gastroenterology* 132: 2131-2157; Burcelin et al., (2007) *J. Nutr.* 137(11 Suppl): 2534S-2538S). The circulation time of the activated GLP-1 is less than 2 minutes due to degradation by a ubiquitous protease enzyme dipeptidyl peptidase 4 (DPP-4) to the inactive form of amino acids 9-37 (Baggio & Drucker (2007) *Gastroenterology* 132: 2131-2157; Holst et al., (2008) *Trends Mol. Med.* 14: 161-168). Evidence suggested that the inactive (9-37) GLP-1 plays a role in clearance of glucose and regulation of cardiovascular function (Drucker, D J, (2006) *Cell Metab.* 3: 153-165; Mannucci & Rotella (2008) *Nutr. Metab. Cardiovasc. Dis.* 18: 639-645; Nauck, M A, (2009) *Eur. J. Intern. Med.* 20 (Suppl 2): S303-308). GLP-1 acts via a cell surface receptor, GLP-1 receptor (GLP-1R) belonging to the class B family of 7-transmembrane spanning heterotrimeric G-protein coupled receptors (Mayo et al., (2003) *Pharmacol Rev.* 55: 167-194).

GLP-1R is expressed in the pancreatic islet in very high levels (Korner et al., (2007) *J. Nucl. Med.* 48: 736-743). The receptor is also expressed in several other organ sites, including, kidney, heart, lung, and central nervous system (Doyle & Egan (2007) *Pharmacol. Ther.* 113: 546-593). In the pancreatic islet, GLP-1R is predominately located in the β-cells at a density as high as $10^5$-$10^6$ receptormolecules/cell (Korner et al., (2007) *J. Nucl. Med.* 48: 736-743; Wei & Mojsov (1995) *FEBS Letts.* 358: 219-224).

The insulinotropic actions of GLP-1 include insulin secretion and insulin biosynthesis including proinsulin gene expression (Egan et al., (2003) *Diabetes Metab. Res. Rev.* 19: 115-123; Winzell & Ahren (2007) *Pharmacol. Ther.* 116: 437-448). This stimulation of insulin secretion in pancreatic β-cells by GLP-1 is dependent on elevation of plasma glucose. The detailed mechanism by which the GLP-1 stimulates insulin secretion under elevated plasma glucose is not well understood. GLP-1 may act via the GLP-1R to stimulate cyclic AMP formation and activate protein kinase A in pancreatic β-cells. The action of GLP-1 also includes replenishment of the intracellular insulin pool by up-regulating the expression of proinsulin, which includes proinsulin gene transcription and mRNA stability (Doyle & Egan (2007) *Pharmacol. Ther.* 113: 546-593; de Heer et al., (2008) *Diabetologia* 51: 2263-2270; Ahren et al., (2004) *Horm. Metab. Res.* 36: 733-734). It was demonstrated that the production of cAMP and activation of PKA under GLP-1 stimulation activates the transcription activator Pdx that plays an important role in insulin gene transcription (Li et al., (2005) *Diabetes* 54: 482-491). In addition to insulintropic actions, GLP-1 promotes differentiation of progenitor cells to mature β-cells in islet (Yue et al., (2006) *Tissue Eng.* 12: 2105-2116) and also trigger cellular processes in pancreatic β-cells that promote β-cell proliferation and inhibit apoptosis, which consequently leads to an increase in pancreatic β-cell mass and normalizes the β-cell function in pancreas (Doyle & Egan (2007) *Pharmacol. Ther.* 113: 546-593; Klinger et al., (2008) *Diabetes* 57: 584-593; Bonora, E, (2008) *Nutr. Metab. Cardiovasc. Dis.* 18: 74-83).

Rapid degradation of native GLP-1 by DPP-4 hampers the application of the native GLP-1 as a potential diabetes treatment. Substantial efforts were made to develop a diabetes treatment based on the GLP-1 and GLP-1R pathway (Ahren & Schmitz (2004) *Horm. Metab. Res.* 36: 867-876; Salehi & D'Alessio (2006) *Cleve. Clin. J. Med.* 73: 382-389; Arulmozhi & Portha (2006) *Eur. J. Pharm. Sci.* 28: 96-108; McGill, J B (2009) *Postgrad. Med.* 121: 46-45). Most attention has focused on developing GLP-1R agonists and DPP-4 inhibitors (Combettes, M M (2006) *Curr. Opin. Pharmacol.* 6: 598-605; Gromada et al., (2004) *Basic Clin. Pharmacol. Toxicol.* 95: 252-262).

One early GLP-1R agonist is exendin-4, a 39 amino acid GLP-1 analog, purified from the saliva of the lizard *Heloderma suspectum*. Exendin-4 is resistant to DPP-4 cleavage (Deacon, et al., (1998) *Diabetologia* 41: 271-278) resulting in an approximately 3 hour blood circulation time in human. Exendin-4 has been approved by the FDA as a treatment of type 2 diabetes by twice daily injections. However, short blood circulation time limits the effectiveness of the exendin-4 as diabetes treatment.

Several new agents acting as long-lasting GLP-1R agonists are currently undergoing clinical trials. Substitution of two amino acids of GLP-1 and acylation of the peptide with a long chain fatty acid led to development of Liraglutide (Knudsen, L B (2004) J. Med. Chem. 47: 4128-4134; Juhl et al., (2002) *Diabetes* 51: 424-429). Thus, mutations at two amino acids resulted in DPP-4 resistance and acylation led to the binding of the peptide to serum albumin. The resultant peptide has a more than 10 hr blood circulation time. Another DPP-4 resistant and long circulating GLP-1R agonist was developed by substituting the Ala-18 of GLP-1 with D-Ala and then linking it (via maleimidoproprionic acid) to the C-terminal of serum albumin (CJC-1131) (Kim et al., (2003) Diabetes 52: 751-759). Albugon is another serum albumin based GLP-1 agonist (Baggio et al., (2004) Diabetes 53: 2492-2500). In this case the GLP-1 is directly conjugated to the serum albumin.

Most approaches for development of long circulating GLP-1R agonists were based on binding or conjugation to serum albumin. These approaches achieved great successes, but, there are drawbacks. Serum albumin is a protein of about 70 kDa molecular mass. The large molecular size limits its capability of endothelial penetration and tissue penetration. Biodistribution of serum albumin also do not favor pancreas delivery of the agents. Intensive studies revealed that serum albumin stays in circulation for a long time with little up-taken by pancreas, especially by islets (Bent-Hansen, L, (1991) *Acta. Physiol. Scand. Suppl.* 603: 5-10). This property significantly limited the delivery of the agent in response to a transient elevation of blood glucose, such as the situation after meals. There is, therefore, an urgent need to develop GLP-1R agonists by alternative approaches.

SUMMARY

Glucagon-like peptide-1 (GLP-1) is a member of a large family of incretin hormones secreted in nutrient-dependent response. GLP-1 acts on GLP-1 receptor (GLP-1R) that is highly expressed on pancreatic 6-cells. The peptide has great potential for development of diabetes treatment and diagnosis. However, the pharmaceutical effects of the peptide suffer from in vivo instability and short life due to degradation by Dipeptidylpeptidase-1 (DPP-4). The 30 amino acid peptide GLP-1 has been integrated into a stable host protein human calbindin D9k. The fusion protein or engineered protein binds to GLP-1R as demonstrated by immunostaining analyses of GLP-1R expressing cells. In vitro tests with a rat insulinoma 6-cell line RINm5F indicate that the protein has strong activity of stimulating production of intracellular cAMP (the activity is comparable to that of native peptide GLP-1 and exendin-4). Experiments with diabetic db/db mice indicate that the protein demonstrated strong activity in lowering blood glucose with substantial longer activity compared to that of exendin-4. The host protein was a previously engineered Gd-binding protein with high $Gd^{3+}$ affinity and metal selectivity. The proteins of the disclosure exhibits more than 20-fold enhanced R1 and R2 relaxivity compared to that of Gd-DTPA (per $Gd^{3+}$). The protein agents can be useful for both diabetes treatment and GLP-1R receptor targeting MR imaging. The protein has a size about 14 kDa, which enables efficient tissue penetration and retention, and an extended circulation time. The protein is stable, remaining intact and retaining activity after 48 hours incubation with 75% human serum. The protein retains its native folded structure after boiling for ten minutes forming the basis of an experimental protocol for large scale production of the fusion protein (>30 mg/l bacterial culture). No toxicity has been observed with tests on mice.

One aspect of the disclosure, therefore, provides a fusion protein comprising a first peptide characterized by selectively binding to a site of a target cell and linked to a second peptide, where the fusion protein is more stable than the first peptide alone.

In embodiments of this aspect of the disclosure, the fusion protein may further comprise a detectable label attached thereto.

In some embodiments of this aspect of the disclosure, the first peptide of the fusion protein may be glucagon-like peptide-1 (GLP-1), glucagon-like peptide-1 (GLP-1) (7-36), or glucagon-like peptide-1 (GLP-1) (9-36), or a conservative variant thereof.

In one embodiment of the disclosure, the first peptide of the fusion protein has the amino acid sequence HAEGTFTSDVSSYLEGQAAKEFIAWLVKGR (SEQ ID NO: 1), and the second peptide has the amino acid sequence MSTKKSPEELKRIFEKYAAKEGDPDQL-SKDELKLLIQAEFPSLLKGPNTLDDLFQELDKNG (SEQ ID NO: 2).

One aspect of the disclosure, therefore, provides an engineered protein comprising a first peptide characterized by selectively binding to a site of a target cell and linked to a second peptide, where the fusion protein is more stable than the first peptide alone.

In embodiments of this aspect of the disclosure, the engineered protein may further comprise a detectable label attached thereto.

In some embodiments of this aspect of the disclosure, the engineered protein of the fusion protein may be glucagon-like peptide-1 (GLP-1), glucagon-like peptide-1 (GLP-1) (7-36), or glucagon-like peptide-1 (GLP-1) (9-36), or a conservative variant thereof.

In one embodiment of the disclosure, the first peptide of the engineered protein has the amino acid sequence HAEGTFTSDVSSYLEGQAAKEFIAWLVKGR (SEQ ID NO: 1), and the second peptide has the amino acid sequence MSTKKSPEELKRIFEKYAAKEGDPDQL-SKDELKLLIQAEFPSLLKGPNTLDDLFQELDKNG (SEQ ID NO: 2).

Another aspect of the disclosure provides methods of regulating glucose metabolism by an animal or human cell, comprising: contacting an animal or human cell with a composition comprising a protein, said fusion protein comprising a first peptide linked to a second peptide, where the protein is more stable than the first peptide alone, and where the first peptide is glucagon-like peptide-1 (GLP-1) or a variant thereof; the second peptide is part of calbindin D9k, an amino acid sequence variant thereof, or a modified variant thereof; and where the fusion protein selectively binds to a GLP-1 receptor of the target cell, thereby regulating the activity of the receptor and glucose metabolism by an cell.

Still another aspect of the disclosure provides imaging probes, where the probe is a protein comprising: a first peptide characterized by selectively binding to a site of the target cell and linked to a second peptide, wherein the second peptide increases the stability of the first peptide linked thereto; and a detectable label.

In one embodiment of this aspect of the disclosure, the first peptide of the protein can have the amino acid sequence (SEQ ID NO: 1), the second peptide can have an amino acid sequence MSTKKSPEELKRIFEKYAAKEGDPDQL-SKDELKLLIQAEFPSLLKGPNTLDDLFQELDKNG (SEQ ID NO: 2), and the label is gadolinium (Gd$^+$), whereby the label is detectable by MRI, and wherein the fusion protein binding site is a GLP-1 receptor of a pancreatic cell.

Yet another aspect of the disclosure provides methods of enhancing imaging contrast, comprising: (i) delivering to a target cell an imaging probe comprising a protein, wherein the fusion probe comprises: a first peptide characterized by selectively binding to a site of the target cell and linked to a second peptide, wherein the protein is more stable than the first peptide alone; and a detectable label; and (ii) detecting a signal from the label, thereby determining the presence of the site of protein binding of the target cell.

BRIEF DESCRIPTION OF THE DRAWINGS

Further aspects of the present disclosure will be more readily appreciated upon review of the detailed description of its various embodiments, described below, when taken in conjunction with the accompanying drawings.

Figure 1:
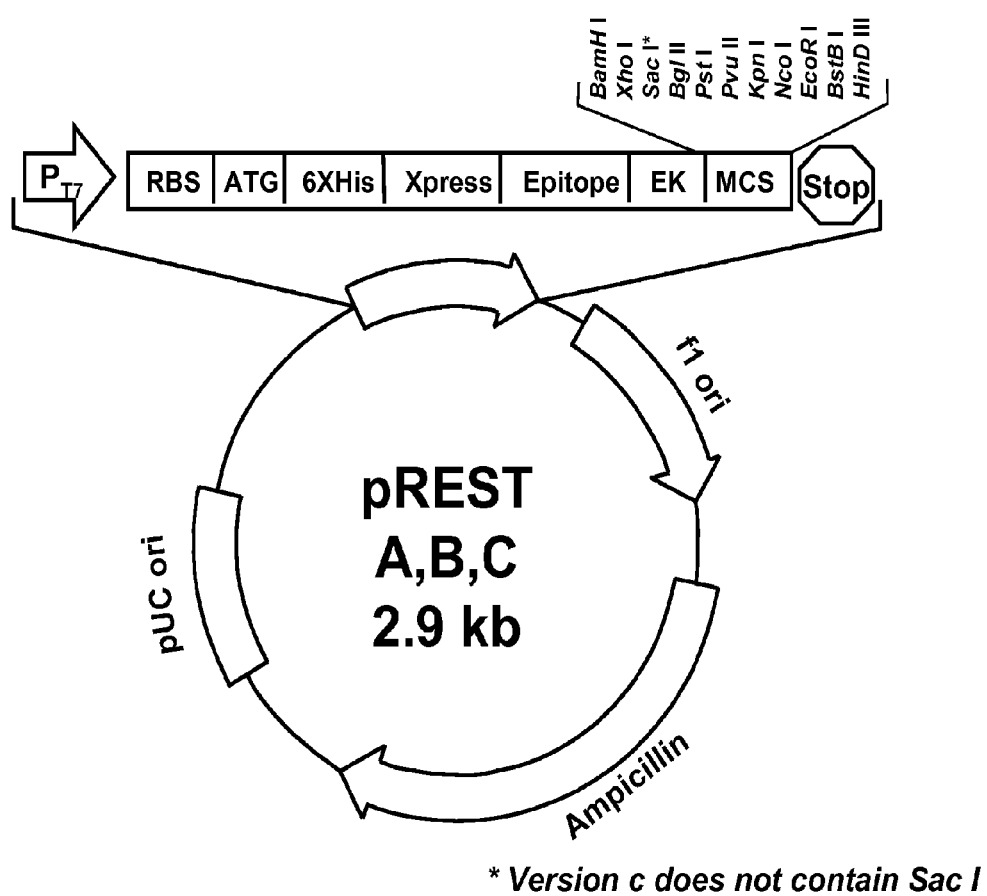
FIG. 1 illustrates the plan of the plasmid vector pRSETb.

The drawings are described in greater detail in the description and examples below.

The details of some exemplary embodiments of the methods and systems of the present disclosure are set forth in the description below. Other features, objects, and advantages of the disclosure will be apparent to one of skill in the art upon examination of the following description, drawings, examples and claims. It is intended that all such additional systems, methods, features, and advantages be included within this description, be within the scope of the present disclosure, and be protected by the accompanying claims.

DETAILED DESCRIPTION

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

As used herein, the following terms have the meanings ascribed to them unless specified otherwise. In this disclosure, "comprises," "comprising," "containing" and "having" and the like can have the meaning ascribed to them in U.S. Patent law and can mean "includes," "including," and the like; "consisting essentially of" or "consists essentially" or the like, when applied to methods and compositions encompassed by the present disclosure refers to compositions like those disclosed herein, but which may contain additional structural groups, composition components or method steps (or analogs or derivatives thereof as discussed above). Such additional structural groups, composition components or method steps, etc., however, do not materially affect the basic and novel characteristic(s) of the compositions or methods, compared to those of the corresponding compositions or methods disclosed herein. "Consisting essentially of" or "consists essentially" or the like, when applied to methods and compositions encompassed by the present disclosure have the meaning ascribed in U.S. Patent law and the term is open-ended, allowing for the presence of more than that which is recited so long as basic or novel characteristics of that which is recited is not changed by the presence of more than that which is recited, but excludes prior art embodiments.

Prior to describing the various embodiments, the following definitions are provided and should be used unless otherwise indicated.

DEFINITIONS

The term "cell or population of cells" as used herein refers to an isolated cell or plurality of cells excised from a tissue or grown in vitro by tissue culture techniques. Most particularly, a population of cells refers to cells in vivo in a tissue of an animal or human.

The term "contacting a cell or population of cells" as used herein refers to delivering a peptide or probe according to the present disclosure to an isolated or cultured cell or population of cells or administering the probe in a suitable pharmaceutically acceptable carrier to the target tissue of an animal or human. Administration may be, but is not limited to, intravenous delivery, intraperitoneal delivery, intramuscularly, subcutaneously or by any other method known in the art. One advantageous method is to deliver directly into a blood vessel leading immediately into a target organ or tissue such as a pancreas, thereby reducing dilution of the probe in the general circulatory system.

The term "dye" as used herein refers to any reporter group whose presence can be detected by its light absorbing or light emitting properties. For example, Cy5 is a reactive water-soluble fluorescent dye of the cyanine dye family. Cy5 is fluorescent in the red region (about 650 to about 670 nm). It may be synthesized with reactive groups on either one or both of the nitrogen side chains so that they can be chemically linked to either nucleic acids or protein molecules. Labeling is done for visualization and quantification purposes. Cy5 is excited maximally at about 649 nm and emits maximally at about 670 nm, in the far red part of the spectrum; quantum yield is 0.28. FW=792. Suitable fluorophores (chromes) for the probes of the disclosure may be selected from, but not intended to be limited to, fluorescein isothiocyanate (FITC, green), cyanine dyes Cy2, Cy3, Cy3.5, Cy5, Cy5.5 Cy7, Cy7.5 (ranging from green to near-infrared), Texas Red, and the like. Derivatives of these dyes for use in the embodiments of the disclosure may be, but are not limited to, Cy dyes (Amersham Bioscience), Alexa Fluors (Molecular Probes Inc.,), HILYTE™ Fluors (AnaSpec), and DYLITE™ Fluors (Pierce, Inc).

The term "fluorescence" as used herein refers to a luminescence that is mostly found as an optical phenomenon in cold bodies, in which the molecular absorption of a photon triggers the emission of a photon with a longer (less energetic) wavelength. The energy difference between the absorbed and emitted photons ends up as molecular rotations, vibrations or heat. Sometimes the absorbed photon is in the ultraviolet range, and the emitted light is in the visible range, but this depends on the absorbance curve and Stokes shift of the particular fluorophore.

By "detectably labeled" is meant that a protein or nucleic acid, or a fragment thereof, contains a moiety that is radioactive, or that is substituted with a fluorophore, or that is substituted with some other molecular species that elicits a physical or chemical response that can be observed or detected by the naked eye or by means of instrumentation such as, without limitation, scintillation counters, colorimeters, UV spectrophotometers and the like. As used herein, a "label" or "tag" can refer to a molecule that, when appended by, for example, without limitation, covalent bonding or hybridization, to another molecule, for example, also without limitation, a peptide, provides or enhances a means of detecting the other molecule. A fluorescence or fluorescent label or tag emits detectable light at a particular wavelength when excited at a different wavelength. A radiolabel or radioactive tag emits radioactive particles detectable with an instrument such as, without limitation, a scintillation counter. The term "label" as used herein may refer to any moiety that may be linked to the compounds of the present disclosure and which may be used to provide a detectable image including, but not limited to fluorescent dyes, MRI agents such as $Gd^{3+}$, $F^{19}$, and the like; PET agents such as, but not limited to, $F^{18}$, $I^{125}$, and $Cu^{64}$; or SPECT agents such as $I^{131}$.

The term "pharmaceutically acceptable carrier" as used herein refers to a diluent, adjuvant, excipient, or vehicle with which a heterodimeric probe of the disclosure is administered and which is approved by a regulatory agency of the Federal or a state government or listed in the U.S. Pharmacopeia or other generally recognized pharmacopeia for use in animals, and more particularly in humans. Such pharmaceutical carriers can be liquids, such as water and oils, including those of petroleum, animal, vegetable or synthetic origin, such as peanut oil, soybean oil, mineral oil, sesame oil and the like. The pharmaceutical carriers can be saline, gum acacia, gelatin, starch paste, talc, keratin, colloidal silica, urea, and the like. When administered to a patient, the heterodimeric probe and pharmaceutically acceptable carriers can be sterile. Water is a useful carrier when the heterodimeric probe is administered intravenously. Saline solutions and aqueous dextrose and glycerol solutions can also be employed as liquid carriers, particularly for injectable solutions. Suitable pharmaceutical carriers also include excipients such as glucose, lactose, sucrose, glycerol monostearate, sodium chloride, glycerol, propylene, glycol, water, ethanol and the like. The present compositions, if desired, can also contain minor amounts of wetting or emulsifying agents, or pH buffering agents. The present compositions advantageously may take the form of solutions, emulsion, sustained-release formulations, or any other form suitable for use.

The term "polymerase chain reaction" or "PCR" as used herein refers to a thermocyclic, polymerase-mediated, DNA amplification reaction. A PCR typically includes template molecules, oligonucleotide primers complementary to each strand of the template molecules, a thermostable DNA polymerase, and deoxyribonucleotides, and involves three distinct processes that are multiply repeated to effect the amplification of the original nucleic acid. The three processes (denaturation, hybridization, and primer extension) are often performed at distinct temperatures, and in distinct temporal steps. In many embodiments, however, the hybridization and primer extension processes can be performed concurrently. The nucleotide sample to be analyzed may be PCR amplification products provided using the rapid cycling techniques described in U.S. Pat. Nos. 6,569,672; 6,569,627; 6,562,298; 6,556,940; 6,569,672; 6,569,627; 6,562,298; 6,556,940; 6,489,112; 6,482,615; 6,472,156; 6,413,766; 6,387,621; 6,300,124; 6,270,723; 6,245,514; 6,232,079; 6,228,634; 6,218,193; 6,210,882; 6,197,520; 6,174,670; 6,132,996; 6,126,899; 6,124,138; 6,074,868; 6,036,923; 5,985,651; 5,958,763; 5,942,432; 5,935,522; 5,897,842; 5,882,918; 5,840,573; 5,795,784; 5,795,547; 5,785,926; 5,783,439; 5,736,106; 5,720,923; 5,720,406; 5,675,700; 5,616,301; 5,576,218 and 5,455,175, the disclosures of which are incorporated by reference in their entireties. Other methods of amplification include, without limitation, NASBR, SDA, 3SR, TSA and rolling circle replication. It is understood that, in any method for producing a polynucleotide containing given modified nucleotides, one or several polymerases or amplification methods may be used. The selection of optimal polymerization conditions depends on the application.

The term "polymerase" as used herein refers to an enzyme that catalyzes the sequential addition of monomeric units to a polymeric chain, or links two or more monomeric units to initiate a polymeric chain. In advantageous embodiments of this invention, the "polymerase" will work by adding monomeric units whose identity is determined by and which is complementary to a template molecule of a specific sequence. For example, DNA polymerases such as DNA pol 1 and Taq polymerase add deoxyribonucleotides to the 3' end of a polynucleotide chain in a template-dependent manner, thereby synthesizing a nucleic acid that is complementary to the template molecule. Polymerases may be used either to extend a primer once or repetitively or to amplify a polynucleotide by repetitive priming of two complementary strands using two primers.

The term "primer" as used herein refers to an oligonucleotide, the sequence of at least a portion of which is complementary to a segment of a template DNA which to be amplified or replicated. Typically primers are used in performing the polymerase chain reaction (PCR). A primer hybridizes with (or "anneals" to) the template DNA and is used by the polymerase enzyme as the starting point for the replication/amplification process. By "complementary" is meant that the nucleotide sequence of a primer is such that the primer can form a stable hydrogen bond complex with the template; i.e., the primer can hybridize or anneal to the template by virtue of the formation of base-pairs over a length of at least ten consecutive base pairs.

The primers herein are selected to be "substantially" complementary to different strands of a particular target DNA sequence. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand.

The term "protein" as used herein refers to a large molecule composed of one or more chains of amino acids in a specific order. The order is determined by the base sequence of nucleotides in the gene coding for the protein. Proteins are required for the structure, function, and regulation of the body's cells, tissues, and organs. Each protein has a unique function.

The term "peptide" as used herein refers to proteins and fragments thereof. Peptides are disclosed herein as amino acid residue sequences. Those sequences are written left to right in the direction from the amino to the carboxy terminus. In accordance with standard nomenclature, amino acid residue sequences are denominated by either a three letter or a single letter code as indicated as follows: Alanine (Ala, A), Arginine (Arg, R), Asparagine (Asn, N), Aspartic Acid (Asp, D), Cysteine (Cys, C), Glutamine (Gln, Q), Glutamic Acid (Glu, E), Glycine (Gly, G), Histidine (His, H), Isoleucine (Ile, I), Leucine (Leu, L), Lysine (Lys, K), Methionine (Met, M), Phenylalanine (Phe, F), Proline (Pro, P), Serine (Ser, S), Threonine (Thr, T), Tryptophan (Trp, W), Tyrosine (Tyr, Y), and Valine (Val, V).

The term "variant" refers to a peptide or polynucleotide that differs from a reference peptide or polynucleotide, but retains essential properties. A typical variant of a peptide differs in amino acid sequence from another, reference peptide. Generally, differences are limited so that the sequences of the reference peptide and the variant are closely similar overall and, in many regions, identical. A variant and reference peptide may differ in amino acid sequence by one or more modifications (e.g., substitutions, additions, and/or deletions). A variant of a peptide includes conservatively modified variants (e.g., conservative variant of about 75, about 80, about 85, about 90, about 95, about 98, about 99% of the original sequence). A substituted or inserted amino acid residue may or may not be one encoded by the genetic code. A variant of a peptide may be naturally occurring, such as an allelic variant, or it may be a variant that is not known to occur naturally.

The term "target" as used herein refers to a peptide, cell, tissue, tumor, etc, for which it is desired to detect. The target peptide may be on a cell surface, the cell being isolated from an animal host, a cultured cell or a cell or population of cells in a tissue of an animal.

The present disclosure includes peptides which are derivable from the naturally occurring sequence of the peptide. A peptide is said to be "derivable from a naturally occurring amino acid sequence" if it can be obtained by fragmenting a naturally occurring sequence, or if it can be synthesized based upon knowledge of the sequence of the naturally occurring amino acid sequence or of the genetic material (DNA or RNA) that encodes this sequence. Included within the scope of the present disclosure are those molecules which are said to be "derivatives" of a peptide. Such a "derivative" or "variant" shares substantial similarity with the peptide or a similarly sized fragment of the peptide and is capable of functioning with the same biological activity as the peptide.

A derivative of a peptide is said to share "substantial similarity" with the peptide if the amino acid sequences of the derivative is at least 80%, at least 90%, at least 95%, or the same as that of either the peptide or a fragment of the peptide having the same number of amino acid residues as the derivative.

The derivatives of the present disclosure include fragments which, in addition to containing a sequence that is substantially similar to that of a naturally occurring peptide may contain one or more additional amino acids at their amino and/or their carboxy termini. Similarly, the invention includes peptide fragments which, although containing a sequence that is substantially similar to that of a naturally occurring peptide, may lack one or more additional amino acids at their amino and/or their carboxy termini that are naturally found on the peptide.

The disclosure also encompasses the obvious or trivial variants of the above-described fragments which have inconsequential amino acid substitutions (and thus have amino acid sequences which differ from that of the natural sequence) provided that such variants have an activity which is substantially identical to that of the above-described derivatives. Examples of obvious or trivial substitutions include the substitution of one basic residue for another (i.e. Arg for Lys), the substitution of one hydrophobic residue for another (i.e. Leu for Ile), or the substitution of one aromatic residue for another (i.e. Phe for Tyr), etc.

Modifications and changes can be made in the structure of the peptides of this disclosure and still obtain a molecule having similar characteristics as the peptide (e.g., a conservative amino acid substitution). For example, certain amino acids can be substituted for other amino acids in a sequence without appreciable loss of activity. Because it is the interactive capacity and nature of a peptide that defines that peptide's biological functional activity, certain amino acid sequence substitutions can be made in a peptide sequence and nevertheless obtain a peptide with like properties.

In making such changes, the hydropathic index of amino acids can be considered. The importance of the hydropathic amino acid index in conferring interactive biologic function on a peptide is generally understood in the art. It is known that certain amino acids can be substituted for other amino acids having a similar hydropathic index or score and still result in a peptide with similar biological activity. Each amino acid has been assigned a hydropathic index on the basis of its hydrophobicity and charge characteristics. Those indices are: isoleucine (+4.5); valine (+4.2); leucine (+3.8); phenylalanine (+2.8); cysteine/cysteine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is believed that the relative hydropathic character of the amino acid determines the secondary structure of the resultant peptide, which in turn defines the interaction of the peptide with other molecules, such as enzymes, substrates, receptors, antibodies, antigens, and the like. It is known in the art that an amino acid can be substituted by another amino acid having a similar hydropathic index and still obtain a functionally equivalent peptide. In such changes, the substitution of amino acids whose hydropathic indices are within ±2 is preferred, those within ±1 are particularly preferred, and those within ±0.5 are even more particularly preferred.

Substitution of like amino acids can also be made on the basis of hydrophilicity, particularly, where the biological functional equivalent peptide or peptide thereby created is intended for use in immunological embodiments. The following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); proline (−0.5±1); threonine (−0.4); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent peptide. In such changes, the substitution of amino acids whose hydrophilicity values are within ±2 is preferred, those within ±1 are particularly preferred, and those within ±0.5 are even more particularly preferred.

As outlined above, amino acid substitutions are generally based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include (original residue: exemplary substitution): (Ala: Gly, Ser), (Arg: Lys), (Asn: Gln, His), (Asp: Glu, Cys, Ser), (Gln: Asn), (Glu: Asp), (Gly: Ala), (His: Asn, Gln), (Ile: Leu, Val), (Leu: Ile, Val), (Lys: Arg), (Met: Leu, Tyr), (Ser: Thr), (Thr: Ser), (Tip: Tyr), (Tyr: Trp, Phe), and (Val: Ile, Leu).

The terms "subject," "individual," "patient," and "host" are used interchangeably herein and refer to any vertebrate, particularly any mammal, and most particularly including human subjects, farm animals, and mammalian pets. The subject may be, but is not necessarily, under the care of a health care professional such as a doctor or veterinarian and may be in need of therapeutic treatment with the compositions of the disclosure.

The term "stability" as used herein refers to when a peptide essentially retains its physical and chemical stability and integrity upon storage and exposure to what would be inactivating conditions, including but not limited to, oxidation, heat denaturation, peptidase cleavage, and the like, and which would substantially reduce or eliminate the biological activity or structural integrity of the peptide compared to when the peptide has not been subject to such conditions.

The term "vector" as used herein means a DNA molecule serving as a vehicle capable of stably carrying exogenous genes into host cells. For useful application, a vector should be replicapable, have a system for introducing itself into a host cell, and possess selectable markers.

DISCUSSION

The present disclosure encompasses methods of stabilizing peptides and polypeptides, especially those in an in vivo environment, thereby extending their half-lives and prolonging their effectiveness as administered therapeutic agents. It has been found that a first peptide desired to be stabilized may be linked to another, more stable second peptide, to form a peptide, and that the stability of the second peptide is conferred to the first. It has been found, for example, that the first peptide may substitute for a domain of the second such as an α-helix domain and still retain its biological activity.

An embodiment of such as substitution is the replacement of a region of the peptide calbindin D9k by the peptide Glucagon-Like Peptide-1 (GLP-1). The resulting grafted, or fusion, protein or engineered, now designated Cal.GLP, retains the biological and physiological activities of GLP-1, which is also now resistant to proteolytic degradation and clearance from the recipient animal's serum. Accordingly, the observed in vivo biological effects of GLP-1 are prolonged. This embodiment of the disclosure, therefore, provides an alternative therapeutic agent for the treatment of type 2 diabetes to those currently available, and which suffer from comparatively short effective periods in a recipient.

Since a proteinaceous agent such as the Cal.GLP protein of the present disclosure is intended to have an extended period in the recipient animal or human subject, a matter of concern is the immunogenicity of the construct that could ultimately lead to inactivation of the administered reagent due to the generation of an adverse immune response. However, Cal.GLP product of the disclosure has a low immunogenicity, indicating that any diminution of the agent activity will be less likely as a result of immune clearance.

Another aspect of the disclosure provides methods for modifying the constructs to extend even further their half-lives. In exemplary embodiments of the disclosure, therefore, variants of the protein Cal.GLP were constructed wherein a residue or residues were identified that could be substituted and provide an attachment site for a modifying group such as, but not limited to, a polyethylene glycol (PEG) group.

Stabilization of the protein by insertion of a peptide into, or substituting, a domain of another peptide, using the methods of the disclosure, further allows the construction of stabilized imaging contrast agents that have extended half-lives that can allow for a greater concentration of the agent in a targeted tissue. Accordingly, the contrast and sensitivity of the imaging is enhanced, allowing the detection of small cell masses in a tissue that would be otherwise be overlooked such as, but not limited to, β-cell masses in the pancreas.

For example, the Cal.GLP protein can selectively bind to the GLP-R found on pancreatic β-cells. The calbindin moiety of this enhanced stability protein retains the ability to bind a metal nuclide such as $Gd^+$, even though a region of the calbindin has been replaced by the GLP-1 peptide. The increased stability conferred on the GLP allows for the construct to be concentrated in the islets of the pancreas of a subject animal over an extended period.

Accordingly, GLP-1 has now been modified by combining with a stable host protein, human Calbindin D9k or a portion thereof, to increase the molecular weight of GLP-1, stabilize the short peptide structure mobility, and protect the peptide from DPP4 degradation, thereby increasing the circulating half-life. Furthermore, protein PEGylation was pursued to reduce the protein immunogenicity and optimize the protein biodistribution. Thus, the Calbindin D9k-GLP-1 protein was successfully cloned into a pRSETb plasmid vector and expressed in E. coli BL21 (DE3) pLysS. The protein was purified by heat shock followed by Q-column (GE Healthcare).

The condition of cysteine site-specific PEGylation was optimized. A cell-based cAMP assay indicates that both the protein and PEGylated variant thereof can elevate RINm5F cells' intracellular cAMP level through a dose-dependant pattern with a reduced $IC_{50}$ by comparing GLP-1 peptide in vitro; however, wild-type human Calbindin D9k cannot stimulate RINm5F cells to increase intracellular cAMP.

Thus, the protein and the PEGylated variant thereof retain the ability to recognize and activate GLP-1 receptors. In vitro, a protein serum stability test, by incubating proteins in 50% mice serum, indicated both the protein and the PEGylated variant were serum stable at 37° C. for 3 hours, the protein showing little degradation even up to 24 hours. However, much degradation was observed for PEGylated protein, possibly caused by detachment of the PEGylation agent from the protein.

The GLP-1 was grafted into a stable host protein Calbindin D9k on the basis that: (1) grafting the GLP-1 into a stable host protein would stabilize the secondary structure of the peptide and the entire protein. Since helical structure is required for the biological activity of GLP-1 (Thornton & Gorenstein (1994) Biochemistry 33: 3532-3539), stabilizing the structure of the peptide and the protein should enhance its activity; (2) grafting the GLP-1 into a stable host protein would likely result in a folded protein that has strong resistance to DPP-4 cleavage; and (3) grafting GLP-1 into a stable host protein would substantially increase its blood circulation time, leading to prolonged effects.

Figure 6:
FIG. 6 schematically illustrates the design of Cal.GLP (right) from Calbindin D9k.

Calbindin D9k, or a portion thereof, was developed to include $Gd^{3+}$ binding sites. The developed calbindin D9k functioned as an MRI contrast agent with a 20-fold increase in both R1 and R2 relaxivity (Yang et al., (2008) J. Am. Chem. Soc. 130: 9260-9267, incorporated herein by reference in its entirety). Previous studies have also demonstrated long blood circulation time of the protein (Wild et al., (2004) Diabetes Care 27: 1047-1053). The GLP-1 was grafted into the host protein calbindin D9k by replacing a C-terminal helix, as shown in FIG. 6, which allows the protein be targeted to GLP-1 receptor. The newly-generated protein is referred to herein as Cal.GLP. Additional details regarding CA1.CD2 are disclosed in patent application PCT/US2009/039276, which is incorporated herein by reference in its entirety.

One embodiment of the disclosure, therefore, provides a dual-function protein agent for use as both a GLP-1R agonist and as a GLP-1R targeted MRI contrast agent with very high MRI contrast enhancing capability (20-fold increase in R1 and R2 relaxivity compared to those of Gd-DTPA) per $Gd^{3+}$. The protein is resistant to DPP-4 cleavage (stable in 75% human serum for at least 48 hours), allowing the in vivo GLP-1R agonist applications. The relatively small size (approximately 12 kDa) of the protein compared to serum albumin enables good tissue penetration and retention properties and relatively long blood circulation time, which can provide a great benefit for targeting GLP-1R in vivo. The cell-based in vitro tests have demonstrated that the protein has bioactivity comparable to that of exendin-4, indicating that a GLP-1R agonist has been created. Tests with diabetic mice suggested a strong and lasting in vivo activity in lowering blood glucose of the protein.

The feasibility of β-cell MR imaging by targeting GLP-1R has been demonstrated by conjugation of DTPA to exendin-4 that provided β-cell specific contrast enhancements (Gotthardt et al., (2006) Regul. Pept. 137: 162-167). Embodiments of the protein agent of the disclosure exhibits 20 fold enhanced contrast capability compared to Gd-DTPA. Our protein agent also has a favorable blood circulation property compared to that of exendin-4/DTPA conjugation.

An important aspect of the Cal.GLP protein agent is the proper size of the agent to enable efficient tissue penetration and retention. Thus, it is expected that Cal.GLP protein agent can allow temporal delivery of a higher concentration of the agent to the pancreas compared to those albumin-associated agents. This property is important for diabetes treatments, especially in response to a sudden blood glucose elevation. Circulation and distribution properties can be improved by specific modifications, such as PEGylation or acylation. After PEGylation, the blood circulation time of the parental protein calbindin can be increased to more than 24 hours. Unlike the case of peptide, reduction in bioactivity can be avoided in modifications of the developed protein since the PEGylation site is relatively far away from the bio-active site.

MR Imaging by Targeting GLP-1R:

A property of the embodiments of the protein of the present disclosure is its high affinity for $Gd^{3+}$, which enables a very high MRI contrast enhancement capability, in addition to GLP-1R targeting capability. These features support the application of the agent as a MRI contrast agent for GLP-1R targeted pancreatic β-cell imaging. There are two issues that are addressed regarding MR imaging β-cells by targeting GLP-1R. (1) Is receptor number enough to provide strong MRI contrast enhancements at current detection capabilities e.g., at or close to clinical field strength and imaging sequence? (2) Is targeting GLP-1R specific enough for pancreatic β-cell imaging? Success in MR imaging of pancreatic β-cells with exendin-4 and Gd-DTPA conjugation can address the first question (Gotthardt et al., (2006) Regul. Pept. 137: 162-167). Since the agents of the present disclosure are about 20-fold higher in contrast enhancement capability (relaxivity) compared to that of Gd-DTPA, and have a relatively longer circulation time, embodiments of the agents of the present disclosure can provide advantages over the exendin-4 and Gd-DTPA conjugates in MR imaging of GLP-1R. In addition, the GLP-1 receptor number on pancreatic β-cells (about $10^5$/cell) (Korner et al., (2007) *J. Nucl. Med.* 48: 736-743) is not substantially less than the HER2 levels on the SKOV3 cells (about $8 \times 10^5$/cell) (Ross et al., (2004) *Expert Rev. Mol. Diagn.* 4: 169-188). Strong HER2-specific contrast enhancement has been observed with the protein contrast agents disclosed herein that fused with a HER2-targeting affibody in imaging SKOV3 tumor in mouse xenograft model. The results from HER2 targeting MR imaging supported the feasibility of targeting GLP-1R in pancreatic β-cell imaging.

Therefore, GLP-1R is a useful β-cell specific molecular marker in the pancreas islet. It is known that GLP-1R is also expressed in many other organs, such as heart, lung, and central nervous system. The expression of receptor in other organ sites provides a comparative control for imaging assessment of pancreatic β-cells, as the imaging of GLP-1R at other organ sites can be used as a reference when the GLP-1R targeted imaging contrast enhancement in pancreas decreases under diabetic conditions.

Immunogenicity:

One concern for in vivo applications is the possibility of the immunogenicity of all protein therapy and diagnostic agents. The immune response of protein agent CA1.CD2, disclosed in PCT/US2009/039276 and incorporated herein by reference in its entirety, was tested in rabbits. Without adjuvant, no significant immuno-responses were observed after initial injection and followed by three boosters over a two month period. PEGylation of the protein greatly reduced the antibody production even with use of adjuvant. The Cal.GLP is derived from human calbindin D9k. The GLP-1 from rat and human are identical (Wang et al., (1999) Cell 97: 791-803). Thus, it is to be expected that the protein will not be immunogenetic in human.

One aspect of the disclosure, therefore, provides a fusion protein comprising a first peptide characterized by selectively binding to a site of a target cell and linked to a second peptide, wherein the protein is more stable than the first peptide alone.

In embodiments of this aspect of the disclosure, the fusion protein may further comprise a detectable label attached thereto.

In some embodiments of this aspect of the disclosure, the first peptide of the fusion protein may be glucagon-like peptide-1 (GLP-1), glucagon-like peptide-1 (GLP-1) (7-36), or glucagon-like peptide-1 (GLP-1) (9-36), or a conservative variant thereof.

In some embodiments of this aspect of the disclosure, the second peptide can be calbindin D9k, an amino acid sequence variant thereof, or a modified variant thereof.

In an embodiment of the disclosure, the first peptide of the fusion protein is glucagon-like peptide-1 (GLP-1) (9-36) and the second peptide can be part of or all of calbindin D9k, an amino acid sequence variant thereof, or a modified variant thereof.

In some embodiments of this aspect of the disclosure, the first peptide can have the amino acid sequence HAEGTFTSDVSSYLEGQAAKEFIAWLVKGR (SEQ ID NO: 1), or a conservative variant thereof, and the second peptide can have an amino acid sequence selected from the group consisting of: MSTKKSPEELKRIFEKYAAKEGDPDQL-SKDELKLLIQAEFPSLLKGPNTLDDLFQELDKNG (SEQ ID NO: 2), MSTKKSPEELKRIFEKYAAKEGDP-DQLSKDELKLLIQAEFPCLLKGPNTLDDLFQELDKNG (SEQ ID NO: 3), MSTKKSPCELKRIFEKYAAKEGDP-DQLSKDELKLLIQAEFPSLLKGPNTLDDLFQELDKNG (SEQ ID NO: 4), MSTKKSPEELKRIFEKYAAKEGDPD-DLSKDELKLLIQAEFPCLLKGPNTLDDLFQELDKNG (SEQ ID NO: 17), and conservative variants thereof.

In the embodiments of this aspect of the disclosure, the fusion protein may further comprise at least one polyethylene glycol moiety conjugated thereto.

In one embodiment of the disclosure, the first peptide of the fusion protein has the amino acid sequence HAEGTFTSDVSSYLEGQAAKEFIAWLVKGR (SEQ ID NO:1), and the second peptide has the amino acid sequence MST-KKSPEELKRIFEKYAAKEGDPDQL-SKDELKLLIQAEFPSLLKGPNTLDDLFQELDKNG (SEQ ID NO: 2).

In the embodiments of this aspect of the disclosure, the first peptide can replace a region of the second peptide.

In the embodiments of this aspect of the disclosure, the first peptide can be a peptide ligand of a receptor, and wherein the fusion protein regulates the activity of the receptor when said fusion protein is bound to the receptor.

One aspect of the disclosure, therefore, provides an engineered protein comprising a first peptide characterized by selectively binding to a site of a target cell and linked to a second peptide, wherein the protein is more stable than the first peptide alone.

In embodiments of this aspect of the disclosure, the engineered protein may further comprise a detectable label attached thereto.

In some embodiments of this aspect of the disclosure, the first peptide of the engineered protein may be glucagon-like peptide-1 (GLP-1), glucagon-like peptide-1 (GLP-1) (7-36), or glucagon-like peptide-1 (GLP-1) (9-36), or a conservative variant thereof.

In some embodiments of this aspect of the disclosure, the second peptide can be calbindin D9k, an amino acid sequence variant thereof, or a modified variant thereof.

In an embodiment of the disclosure, the first peptide of the engineered protein is glucagon-like peptide-1 (GLP-1) (9-36) and the second peptide can be part of or all of calbindin D9k, an amino acid sequence variant thereof, or a modified variant thereof.

In some embodiments of this aspect of the disclosure, the first peptide can have the amino acid sequence HAEGTFTSDVSSYLEGQAAKEFIAWLVKGR (SEQ ID NO: 1), or a conservative variant thereof, and the second peptide can have an amino acid sequence selected from the group consisting of: MSTKKSPEELKRIFEKYAAKEGDPDQL-SKDELKLLIQAEFPSLLKGPNTLDDLFQELDKNG (SEQ ID NO: 2), MSTKKSPEELKRIFEKYAAKEGDP-DQLSKDELKLLIQAEFPCLLKGPNTLDDLFQELDKNG (SEQ ID NO: 3), MSTKKSPCELKRIFEKYAAKEGDP-DQLSKDELKLLIQAEFPSLLKGPNTLDDLFQELDKNG (SEQ ID NO: 4), MSTKKSPEELKRIFEKYAAKEGDPD-DLSKDELKLLIQAEFPCLLKGPNTLDDLFQELDKNG (SEQ ID NO: 17), and conservative variants thereof.

In the embodiments of this aspect of the disclosure, the engineered protein may further comprise at least one polyethylene glycol moiety conjugated thereto.

In one embodiment of the disclosure, the first peptide of the engineered protein has the amino acid sequence HAEGTFTSDVSSYLEGQAAKEFIAWLVKGR (SEQ ID NO:1), and the second peptide has the amino acid sequence MST-KKSPEELKRIFEKYAAKEGDPDQL-SKDELKLLIQAEFPSLLKGPNTLDDLFQELDKNG (SEQ ID NO: 2).

In the embodiments of this aspect of the disclosure, the first peptide can replace a region of the second peptide.

In the embodiments of this aspect of the disclosure, the first peptide can be a peptide ligand of a receptor, and wherein the engineered protein regulates the activity of the receptor when said fusion protein is bound to the receptor.

Another aspect of the disclosure provides methods of regulating glucose metabolism by an animal or human cell, comprising: contacting an animal or human cell with a composition comprising a fusion protein, said fusion protein comprising a first peptide linked to a second peptide, wherein the protein is more stable than the first peptide alone, and where the first peptide can be glucagon-like peptide-1 (GLP-1) or a variant thereof; the second peptide can be part of or all of calbindin D9k, an amino acid sequence variant thereof, or a modified variant thereof; and where the fusion protein selectively binds to a GLP-1 receptor of the target cell, thereby regulating the activity of the receptor and glucose metabolism by an cell.

In some embodiments of this aspect of the disclosure, the first peptide can have the amino acid sequence HAEGTFTSDVSSYLEGQAAKEFIAWLVKGR (SEQ ID NO: 1), or a conservative variant thereof, and the second peptide can have an amino acid sequence selected from the group consisting of: MSTKKSPEELKRIFEKYAAKEGDPDQL-SKDELKLLIQAEFPSLLKGPNTLDDLFQELDKNG (SEQ ID NO: 2), MSTKKSPEELKRIFEKYAAKEGDP-DQLSKDELKLLIQAEFPCLLKGPNTLDDLFQELDKNG (SEQ ID NO: 3), MSTKKSPCELKRIFEKYAAKEGDP-DQLSKDELKLLIQAEFPSLLKGPNTLDDLFQELDKNG (SEQ ID NO: 4), MSTKKSPEELKRIFEKYAAKEGDPD-DLSKDELKLLIQAEFPCLLKGPNTLDDLFQELDKNG (SEQ ID NO: 17), and conservative variants thereof.

In embodiments of the methods of this aspect of the disclosure, the fusion protein can further comprise at least one polyethylene glycol moiety conjugated thereto.

In some embodiments, the target cell is an isolated cell.

In other embodiments, target cell can be in a tissue of a subject animal or human, thereby decreasing the plasma glucose of the subject.

In embodiments of the methods of this aspect of the disclosure, the subject animal or human can receive an effective dose of the composition further comprising a pharmaceutically acceptable carrier.

Still another aspect of the disclosure provides imaging probes, where the probe is a fusion protein comprising: a first peptide characterized by selectively binding to a site of the target cell and linked to a second peptide, wherein the second peptide increases the stability of the first peptide linked thereto; and a detectable label.

In the embodiments of this aspect of the disclosure, the label can be detectable by fluorescence, MRI, or PET scanning.

In the embodiments of this aspect of the disclosure, the label can be selected from the group consisting of: a dye, a fluorescent dye, a radiolabel, and a metallic ion.

In the embodiments, the label may be attached to the second peptide of the fusion protein.

In the embodiments the site of fusion protein binding to the target cell can be a receptor on the surface of said cell.

In the embodiments of this aspect of the disclosure, the first peptide of the fusion protein can be a ligand of the fusion protein binding site of the target cell.

In some embodiments of the disclosure, the first peptide of the fusion protein can be glucagon-like peptide-1 (GLP-1) (9-36) and the second peptide can be part of or all of calbindin D9k, an amino acid sequence variant thereof, or a modified variant thereof.

In some embodiments of the disclosure, the first peptide can have the amino acid sequence HAEGTFTSDVS-SYLEGQAAKEFIAWLVKGR (SEQ ID NO: 1), or a conservative variant thereof, and the second peptide has an amino acid sequence selected from the group consisting of: MSTKKSPEELKRIFEKYAAKEGDPDQL-SKDELKLLIQAEFPSLLKGPNTLDDLFQELDKNG (SEQ ID NO: 2), MSTKKSPEELKRIFEKYAAKEGDP-DQLSKDELKLLIQAEFPCLLKGPNTLDDLFQELDKNG (SEQ ID NO: 3), MSTKKSPCELKRIFEKYAAKEGDP-DQLSKDELKLLIQAEFPSLLKGPNTLDDLFQELDKNG (SEQ ID NO: 4), MSTKKSPEELKRIFEKYAAKEGDPD-DLSKDELKLLIQAEFPCLLKGPNTLDDLFQELDKNG (SEQ ID NO: 17), and conservative variants thereof.

In the embodiments of this aspect of the disclosure, the fusion protein can further comprise at least one polyethylene moiety conjugated thereto.

In one embodiment of this aspect of the disclosure, the first peptide of the fusion protein can have the amino acid sequence HAEGTFTSDVSSYLEGQAAKEFIAWLVKGR (SEQ ID NO: 1), the second peptide can have an amino acid sequence MSTKKSPEELKRIFEKYAAKEGDPDQL-SKDELKLLIQAEFPSLLKGPNTLDDLFQELDKNG (SEQ ID NO: 2), and the label is gadolinium (Gd$^+$), whereby the label is detectable by MRI, and wherein the fusion protein binding site is a GLP-1 receptor of a cell of the pancreas.

Yet another aspect of the disclosure provides methods of enhancing imaging contrast, comprising: (i) delivering to a target cell an imaging probe comprising a fusion protein, wherein the fusion probe comprises: a first peptide characterized by selectively binding to a site of the target cell and linked to a second peptide, wherein the protein is more stable than the first peptide alone; and a detectable label; and (ii) detecting a signal from the label, thereby determining the presence of the site of fusion protein binding of the target cell.

In the embodiments of this aspect of the disclosure, the target cell can be in a tissue of a subject animal or human, and the imaging probe can be administered to the subject animal or human as a pharmaceutically acceptable composition.

In embodiments of this aspect of the disclosure, the pharmaceutically acceptable composition may further comprise a pharmaceutically acceptable carrier.

In embodiments of this aspect of the disclosure, the label is detectable by fluorescence, MRI, or PET scanning and the label can be selected from the group consisting of: a dye, a fluorescent dye, a radiolabel, and a metallic ion.

In the embodiments, the label can be attached to the second peptide of the fusion protein.

In the embodiments the site of fusion protein binding can be a receptor on the surface of the target cell and the first peptide of the fusion protein can be a ligand of the fusion protein binding site of the target cell.

In some embodiments of this aspect of the disclosure, the first peptide of the fusion protein can be a glucagon-like peptide-1 (GLP-1) (9-36) and the second peptide can be calbindin D9k, an amino acid sequence variant thereof, or a modified variant thereof.

In some embodiments of this aspect of the disclosure, the first peptide can have the amino acid sequence HAEGTFTS-DVSSYLEGQAAKEFIAWLVKGR (SEQ ID NO: 1), or a conservative variant thereof, and the second peptide can have an amino acid sequence selected from the group consisting of: MSTKKSPEELKRIFEKYAAKEGDPDQL-SKDELKLLIQAEFPSLLKGPNTLDDLFQELDKNG (SEQ ID NO: 2), MSTKKSPEELKRIFEKYAAKEGDP-DQLSKDELKLLIQAEFPCLLKGPNTLDDLFQELDKNG (SEQ ID NO: 3), MSTKKSPCELKRIFEKYAAKEGDP-DQLSKDELKLLIQAEFPSLLKGPNTLDDLFQELDKNG (SEQ ID NO: 4), MSTKKSPEELKRIFEKYAAKEGDPD- DLSKDELKLLIQAEFPCLLKGPNTLDDLFQELDKNG (SEQ ID NO: 17), and conservative variants thereof.

In embodiments of the disclosure, the fusion protein may further comprise at least one polyethylene glycol moiety conjugated thereto.

In some embodiments, the first peptide of the fusion protein can have the amino acid sequence HAEGTFTSDVS-SYLEGQAAKEFIAWLVKGR (SEQ ID NO: 1), the second peptide has an amino acid sequence MST-KKSPEELKRIFEKYAAKEGDPDQL-SKDELKLLIQAEFPSLLKGPNTLDDLFQELDKNG (SEQ ID NO: 2), and the label is gadolinium (Gd$^+$), whereby the label is detectable by MRI, and wherein the fusion protein binding site is a GLP-1 receptor of a cell of the pancreas.

The specific examples below are to be construed as merely illustrative, and not limitative of the remainder of the disclosure in any way whatsoever. Without further elaboration, it is believed that one skilled in the art can, based on the description herein, utilize the present disclosure to its fullest extent. All publications recited herein are hereby incorporated by reference in their entirety.

It should be emphasized that the embodiments of the present disclosure, particularly, any "preferred" embodiments, are merely possible examples of the implementations, merely set forth for a clear understanding of the principles of the disclosure. Many variations and modifications may be made to the above-described embodiment(s) of the disclosure without departing substantially from the spirit and principles of the disclosure. All such modifications and variations are intended to be included herein within the scope of this disclosure, and the present disclosure and protected by the following claims.

The following examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. In an embodiment, the term "about" can include traditional rounding according to significant figures of the numerical value. In addition, the phrase "about 'x' to 'y'" includes "about 'x' to about 'y'".

EXAMPLES

Example 1

Plasmid Construction

A plasmid encoding human Calbindin D9k in the pRSETb vector (illustrated in FIG. 1) was obtained. The amino acid sequence of human GLP-1 is HAEGTFTSDVS-SYLEGQAAKEFIAWLVKGR (SEQ ID NO: 1).

Primers used for polymerase chain reaction (PCR) amplification were:

```
forward
                                       (SEQ ID NO: 5)
5'-CTTGTTCGTGGTCGTGGTGGATCCGGAGGAGCATTTGAGATCTTAGC AAATG-3',
and reverse
                                       (SEQ ID NO: 6)
5'-GAACGTGCCTTCTGCGTGTCCGGAACCCGATTTCAAAAAAGGCTTCA

TCTTC-3'.
```

50 μl of PCR mixture consisted of: plasmid vector 1 μl with the concentration of 0.1 μg/μl, forward and reverse primers 0.3 μl each with the concentration about 0.4 μg/μl; dNTP mixture, 0.5 μl (10 mM); Pfu DNA polymerase, 1 μl; Pfu buffer, 5 μl; and distilled water, 41.9 μl. PCR was carried out for 30 cycles under denaturing-annealing-extension conditions of 94° C. for 30 secs, 55° C. for 1 min, 63° C. for 6 mins respectively.

After the first round of PCR, separated product at certain molecular weight was collected and ligated in a 30 μl mixture consisting of: 25 μl DNA solution, 1 μl ATP (10 mM), 1 μl T4 Ligase, 3 μl ligase buffers at room temperature for 4 hrs. The ligated product was then transformed to *E. coli* JM109. After incubation on ampicillin LB agar plate; a single colony was inoculated into 50 ml sterile LB medium for overnight growth at 37° C. The bacteria were then harvested and the plasmid was abstract.

A second round of PCR was performed using the primers:

```
                                                                        (SEQ ID NO: 7)
forward 5'-GGCCAAGCCGCCAGGGAATTCATTGCATGGCTTGTTCGTGGTCGTGGTGGAT-3'
and (SEQ ID NO: 8)
reverse 5'-TTCGAGGTAGCTGCTTACGTCGCTCGTGAACGTGCCTTCTGCGTGTCC-3'
``` was as described above and for 30 cycles under denaturing-annealing-extension conditions of 94° C. for 30 secs, 55° C. for 1 min, 63° C. for 6 mins, respectively.

Additionally, fusion protein cysteine mutants of the calbindin moiety of the fusion protein were constructed for site-specific PEGylation. The primers used to mutate serine-42 and glutamate8 to cysteine were:

```
Serine42:
                                       (SEQ ID NO: 9)
forward 5'-TGTTTACTCAAAGGTCCAAACACCCTAG-3'

(SEQ ID NO: 10)
reverse 5'-GGGGAATTCAGCCTGAATCAATAG-3'
and
```

-continued

Glutamate8
(SEQ ID NO: 11)
forward 5'-TGTGAACTGAAGAGGATTTTTGAAAAATATG-3'

(SEQ ID NO: 12)
reverse 5'-AGGAGACTTTTTAGTACTCATATG-3'.

The expression vector pRSETb, a plasmid vector with ampicillin resistance and multiple restriction enzyme digestion sites, encodes a His6 tag. However, the purification of fusion protein did not require the tag, which was deleted. The plasmid was further verified by DNA auto-sequencing.

Example 2

Expression and Purification of Fusion Protein

BL21 (DE3) pLysS was used to express the fusion protein. After transformation of the constructed plasmid into BL21 (DE3) pLysS competent cells, bacteria were heat shocked at 42° C. for 90 seconds and incubated in antibiotic-free LB medium at 37° C. for 30 mins, then plated on LB agar plate with ampicillin and incubated at 37° C. overnight. A single colony was picked up the next day and inoculated in 50 ml sterile LB medium with ampicillin. After overnight at 37° C., 20 ml LB medium was transferred into 1 L sterile LB-amp medium. When the medium reached an $A_{600\ nm}$=0.6, the expression was induced by 500 µl IPTG (1 M) for 4 hrs.

1 ml of culture solution was centrifuged, the cell pellet resuspended in 100 µl 1×SDS-PAGE loading buffer, and heated to 100° C. for 10 minutes. A 16% SDS-PAGE gel was used to analyze the expression of the protein.

Bacteria were harvested by centrifuging for 10 mins. Cell pellets were resuspended by 10 mM Tris Buffer (pH7.4), and sonicated for 3 mins and centrifuged at 15,000 rpm for 30 mins. The supernatant was heated at 85° C. for 10 mins and centrifuged again at 15,000 rpm for 30 mins. The supernatant was collected and filtered by 0.45 µm syringe filter.

The filtered protein solution was purified by the Q-COL-UMN™ (GE Healthcare) through the AKTA® FPLC system (GE Healthcare). The column, after protein solution was loaded, was washed by 20 ml 10 mM Tris buffer (pH 7.4), and eluted out with a 0-1 M NaCl in 10 mM Tris buffer (pH7.4) gradient. The protein concentration was then determined by Bio-Rad Assay.

Example 3

Site-Specific PEGylation

After the cysteine-mutated fusion protein was purified, the protein was dialyzed from 10 mM Tris buffer (pH7.4) to PBS buffer (pH7.0). Tris (2-carboxyethyl)phosphine hydrochloride solution (TCEP) was used to reduce the dimerized protein to a monomer. After incubation of the protein and TCEP at room temperature for 30 mins, TCEP was dialyzed out through a concentrator by repeatedly adding PBS buffer for a minimum 10 times of the original volume with 3 kDal membrane under an $N_2$ environment to prevent oxidization). Methoxy-PEG Maleimide-MW 5 kDal (Jenkem Technology) was shaken with the protein solution at 4° C. overnight in nitrogen environment. Dialysis was used to remove the free PEGylation agent. SDS-PAGE and MALDI-TOF-MS were used to determine the molecular weight of the PEGylated protein and PEGylation efficiency.

Example 4

Cell-Based Intracellular cAMP Test

A Lance cAMP 384® Kit (Perkin Elmer, Inc) was used to compare the incretin effects of fusion protein and PEGylated protein. Rat Insulinoma cells (RINm5F) were cultured with RPMI1640 with 10% FBS in 75 $cm^2$ cell culture flasks. Cells are harvested and washed three times with HBSS (Invitrogen Corp.) buffer. A series of 5 µl test protein and 5 µl cell suspension with 5000 cells in stimulation buffer (1×HBSS buffer with 5 mM HEPES, 0.1% BSA and 150 mM IBMX) and Alexa, biotin labeled cAMP antibodies were incubated at 37° C. for 15 mins in 384-well plate. 10 µl of detection mix (615 µl detection buffer with 5/16 µl WU-W8044 and 5/6 µl Biotin-cAMP) was then added, and the plated was covered and incubated at room temperature for 60 mins. A VICTOR$^3$ plated reader (PerkinElmer, Inc.) was used to detect the fluorescence signal at excitation 340 nm and emission 665 nm and 615 nm. The collected data was then analyzed with the equation of F=F665 nm/F615 nm.

Example 5

Protein Serum Stability Test

The fusion protein and PEGylated protein were incubated with mice serum at a ratio 1:1, in 37° C. for 1 hr, 3 hrs and 24 hrs. Samples were then analyzed by 16% SDS-PAGE.

Example 6

Fusion Protein Specific Polyclonal Antibodies Generation

Rabbits were used for antibody generation. Before immunization, a 10 ml bleed was collected as pre-bleeding control. At week 0, 300 µg fusion protein was mixed with complete Freund's adjuvant to form a stable emulsion and were injected subcutaneously in the arena around the shoulders, and intramuscularly into the large muscle of the rear legs. At week 2, another immunization of a mixture of 150 µg fusion proteins and the same amount of complete Freund's adjuvant was injected in a same way. At week 4, a second boost of 150 µg with the same amount of incomplete Freund's adjuvant was injected.

At week 5, the first bleeding was about 20-30 ml. At week 6, a third boost of 150 µg protein with same amount of incomplete Freund's adjuvant was injected as before. At week 7, a second bleeding was collected. At weeks 8 and 10, the fourth boost and final boost were administered, and at weeks 9 and 11, the third and final bleedings were collected. Antibody Screening: After each bleeding, mice serum was clarified by centrifugation. Western blot was used for antibodies screening. Proteins were analyzed by 16% SDS-PAGE, transfer to a PVDF membrane in 1× transfer buff (25 mM Trizma Base, 192 mM glycine, pH8.3). The membrane was incubated in blocking buffer (3% BSA, 0.05% Tween 20, in PBS buffer) overnight at 4° C., washed 3 times with PBS buffer with 0.05% Tween 20 for 10 mins each, and incubated with the serum sample (diluted 1:2000 in blocking buffer) for 60 mins at room temperature. Again, membrane was washed three times with washing buffer and incubated with secondary antibody diluted 1:2000 in blocking buffer for 45 mins at room temperature, and washed as before. Finally, the membrane was detected with Amersham ECL kit.

Example 7

Fusion Protein Expression and Purification

The amino acid sequences of human Calbindin D9k, GLP-1, the fusion protein and two cysteine mutants thereof are listed in Table 1.

TABLE 1

Sequences of the proteins

| Protein/Peptide | Sequences |
| --- | --- |
| Human Calbindin D9k | MSTKKSPEELKRIFEKYAAKEGDPDQLSKDELKLLIQAEFPSLLKGPN TLDDLFQELDKNGDGEVSFEEFQVLVKKISQ (SEQ ID NO: 13) |
| GLP-1 | HAEGTFTSDVSSYLEGQAAKEFIAWLVKGRG (SEQ ID NO: 1) |
| Fusion Protein Cal.GLP | MSTKKSPEELKRIFEKYAAKEGDPDQLSKDELKLLIQAEFPSLLKGP NTLDDLFQELDKNGHAEGTFTSDVSSYLEGQAAKEFIAWLVKGRG (SEQ ID NO: 14) |
| Serine42 variant[a] | MSTKKSPEELKRIFEKYAAKEGDPDQLSKDELKLLIQAEFPCLLKGP NTLDDLFQELDKNGHAEGTFTSDVSSYLEGQAAKEFIAWLVKGRG (SEQ ID NO: 15) |
| Glutamate8 variant[a] | MSTKKSPCELKRIFEKYAAKEGDPDQLSKDELKLLIQAEFPSLLKGP NTLDDLFQELDKNGHAEGTFTSDVSSYLEGQAAKEFIAWLVKGRG (SEQ ID NO: 16) |

[a]Positions of the S42C and E8C variations are indicated in bold underline

Sequence for CalGlp/Q26D:

(SEQ ID NO: 18)
MSTKKSPEELKRIFEKYAAKEGDPDDLSKDELKLLIQAEFPCLLKGP

NTLDDLFQELDKNGHAEGTFTSDVSSYLEGQAAKEFIAWLVKGR

Molecular weight of the fusion protein is 10,289 Dalton, PI 4.97; and the two cysteine mutants molecular weights are 10,305 Dalton, PI 4.97; and 10,263 Dalton, PI 5.13, respectively (ExPASy (Expert Protein Analysis System) proteomics Server of the Swiss Institute of Bioinformatics).

The DNA sequences encoding human Calbindin D9k and GLP-1 fusion protein and mutants were cloned into pRSETb plasmid vector and over-expressed by E. coli BL21 (DE3) pLysS host. High-expression levels of the fusion protein were observed. Taking advantage of high thermal stability, heat shock at 85° C. for 10 mins was performed, and followed by Q-column (GE Healthcare) purification through FPLC system. After two steps of purification, high purity and productive fusion protein was obtained.

Example 8

Cysteine Mutants' Purification and Protein PEGylation

Figure 2A:
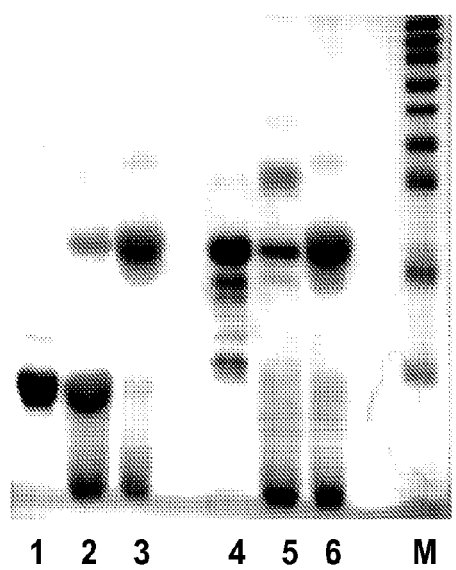
FIG. 2A is a digital image of the analysis of cysteine mutants and protein PEGylation products analyzed by 16% SDS-PAGE and stained by Coomassie blue staining. Lanes 1-3 are non-PEGylated protein, PEGylated protein with PEGylation in non-reduced condition, PEGylated protein with PEGylation in reduced condition, respectively. Proteins were treated by DTT before analysis. Lanes 4-6 are the same protein samples without treatment with DTT.

Cysteine mutants of the human Calbindin D9k-GLP-1 fusion protein were expressed and purified to allow PEGylation. In the non-reduced condition, most of the protein was dimeric (FIG. 2A, Lane 1), molecular weight about 20 KDa; in a reduced condition, most of protein was monomeric (FIG. 2A, Lane 4), molecular weight about 10 KDa.

Figure 2B:
FIG. 2B is a digital image of the same SDS-PAGE as in FIG. 2A stained with iodine. SDS-PAGE gel was treated by 10% BaCl$_2$ for 10 mins ahead of 10 mins staining.
Figure 3:
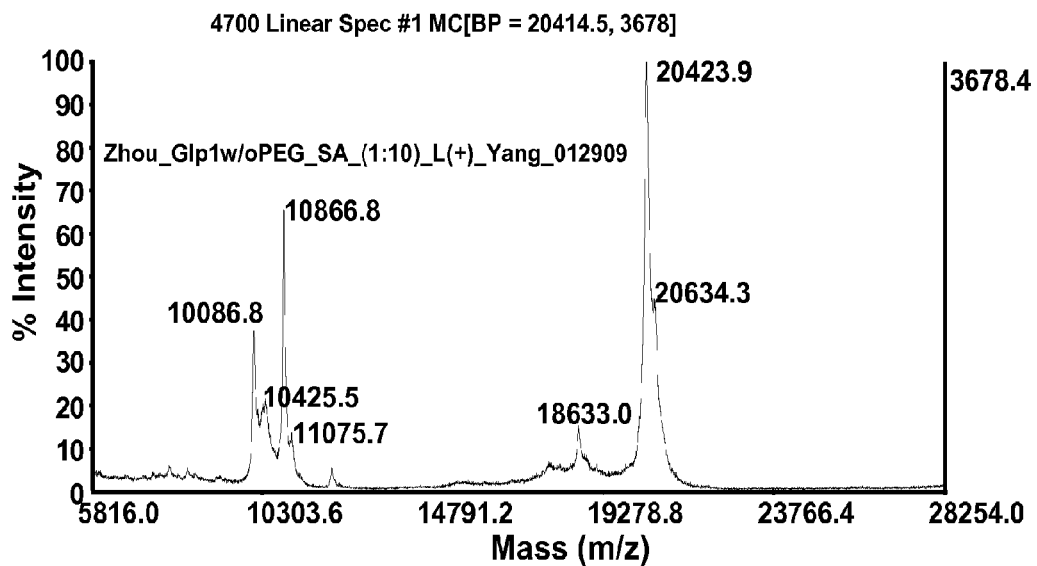
FIG. 3 shows a graph of MALDI-TOF-MS of the S42C mutated fusion protein before PEGylation, which indicated the major proteins were dimers around 20,398 Da and monomers around 10,845 Da.
Figure 4:
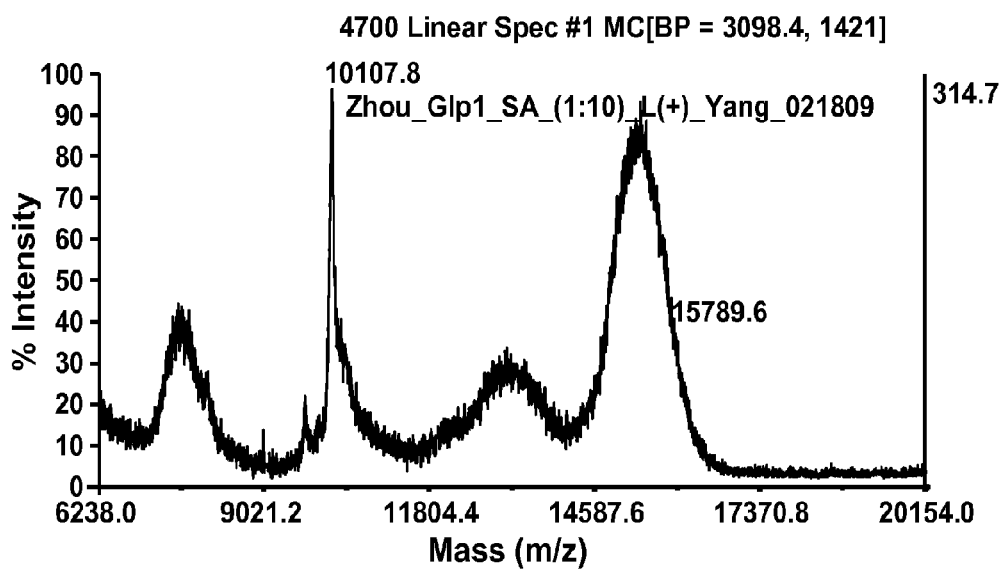
FIG. 4 shows a graph of MALDI-TOF-MS of the S42C mutated fusion protein after PEGylation, which indicated the major protein was PEGylated protein of about 15,302Da.

Cysteine site-specific PEGylation condition was optimized. Protein under reduced conditions (monomer) had better reactivity than as a dimer. The reducing agent was dialyzed out before PEGylation to avoid interference. The PEGylation agent itself was 5 kDa. To verify that the protein band observed in SDS-PAGE was the PEGylated protein, the same SDS-PAGE gel was iodine stained, as shown in FIG. 2B (which will stain the PEG (polyethylene glycol) chain), and proteins were further verified by MALDI-TOF mass spectrometry, as shown in FIGS. 3 and 4).

Example 9

Proteins Cell-Based cAMP Assay

Figure 9:
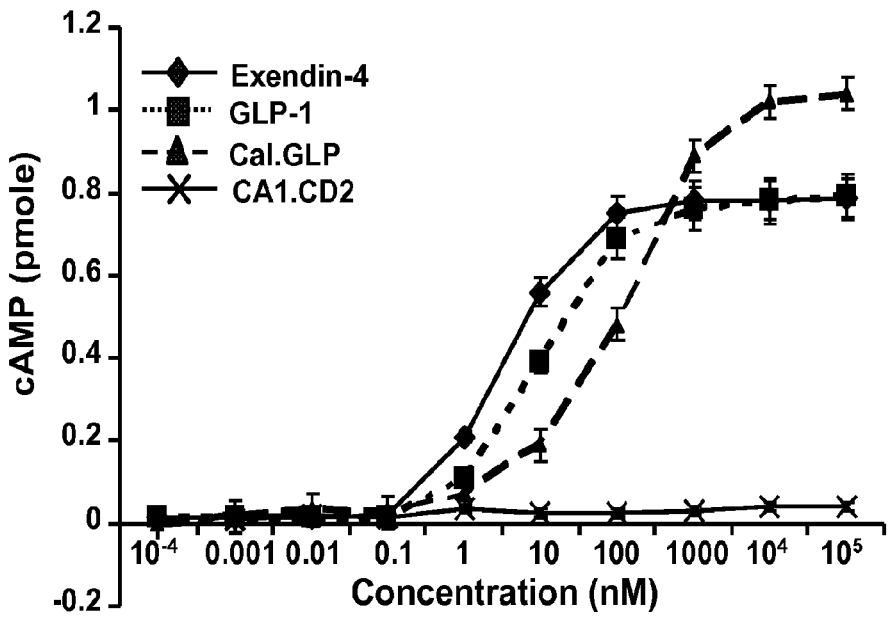
FIG. 9 is a graph showing the cAMP levels in RINm5F cells assayed using the Lance cAMP kit. The cells were treated with various concentrations of Exendin-4 (solid line and diamond), GLP-1 (dot line and rectangle), Cal.GLP (dashed line and triangle), and CA1.CD2 (solid line and cross). The cells were harvested 30 minutes post treatments. Cell lysates were prepared from the harvested cells. The cAMP levels in the lysate were then measured and expressed as pmole values. The error bars represent standard deviations of four times of measurements.

An in vitro cell-based cAMP assay was used to test the fusion protein and PEGylated protein incretin effect. Lance-cAMP 384kit (PerkinElmer, Inc.) was used. GLP-1 and exendin-4 were used as positive controls. The parental protein calbindin D9k was used as a negative control. The experiment demonstrated that the engineered protein CalGLP can increase intracellular cAMP level in rat insulinoma RINm5F cells in a dose dependent pattern, as did the chemically synthesized GLP-1 and exendin-4 peptides, with a $IC_{50}$ around 20 nM ($IC_{50}$ Exendin 4~1 nM, GLP-1 peptide $IC_{50}$: ~4 nM), as shown in FIG. 9. However, wild type human Calbindin D9k alone could not increase cell intracellular cAMP level even at a concentration around 200 μM, which indicated that the fusion protein reactivity was due to the inclusion of GLP-1 and not the host protein itself. These experiments demonstrated that structural change due to the insertion of GLP-1 into a host protein did not eliminate the ability of GLP-1 to recognize and activate the GLP-1 receptor.

Example 10

Figure 16:
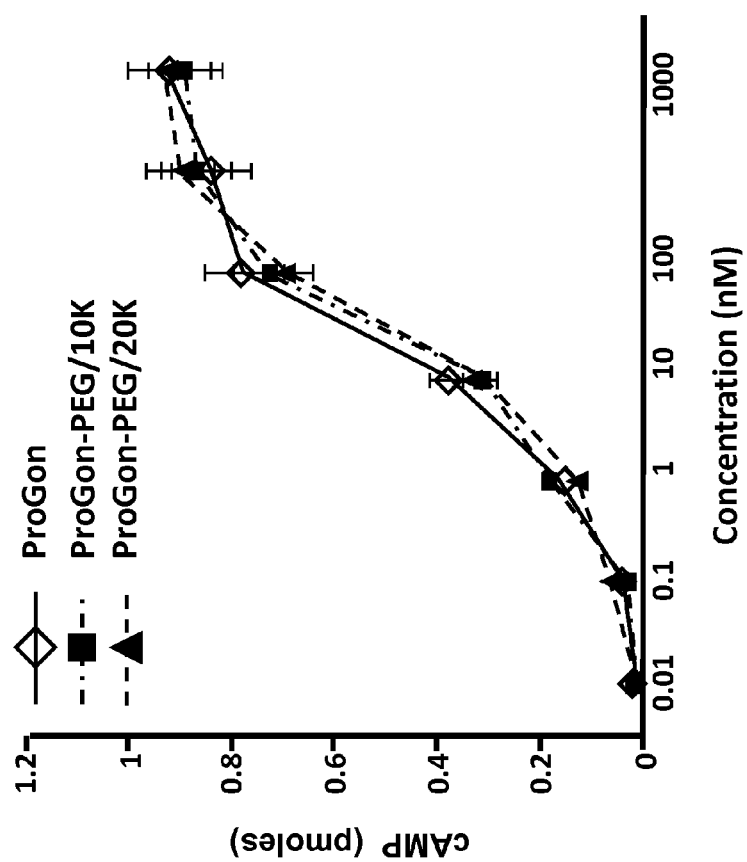
FIG. 16 is a graph showing the effects of CalGLP, and CalGLP-10K on cAMP levels.

The 10 kDa and 20 kDa PEGylated Protein Had Similar Activity of Stimulation of Intracellular cAMP in β-Cells The protein was PEGylated by PEG 10 kDa, and 20 kDa by the method described in Example 3. The effects of the PEGylated proteins and unPEGylated protein in stimulating the cAMP production were examined in rat insulinoma β-cells RINm5F. The cAMP production was analyzed using a commercial cAMP kit (PerkinElmer). It was evident that the 10 kDa and 20 kDa PEGylated proteins had activity comparable to that of unPEGylated protein, as shown in FIG. 16.

Example 11

Protein Serum Stability Test

Figure 5:
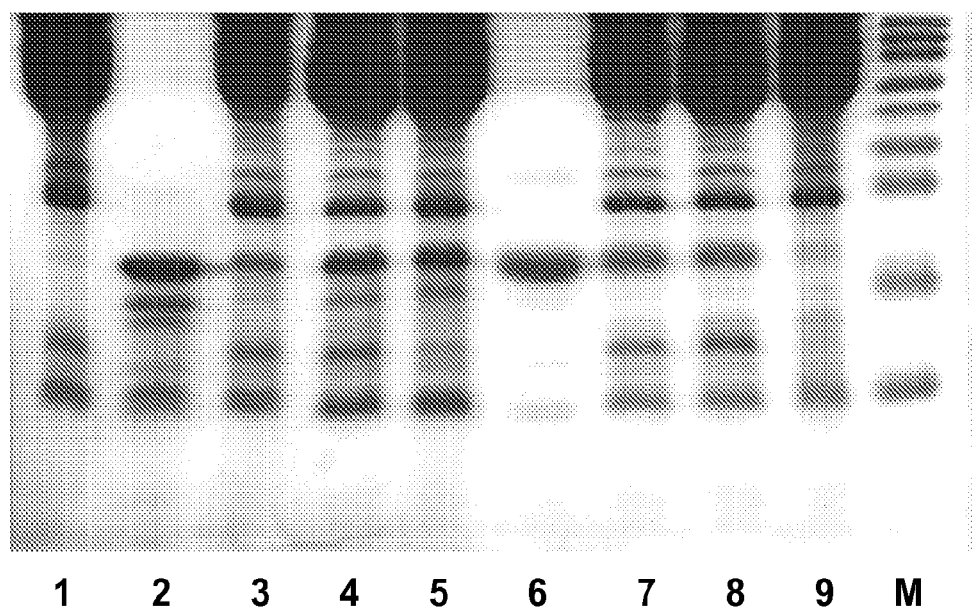
FIG. 5 is a digital image of a gel analysis of a protein serum stability test. A 16% SDS-PAGE without DTT was used to analysis the protein level after incubation with mice serum for certain time. Lane 1: mice serum only; Lane 2: fusion protein only; Lanes 3-5: fusion protein incubated with 50% serum for 1 hr, 3 hrs, and 24 hrs respectively; Lane 6: PEGylated protein only; Lanes 7-9: PEGylated protein incubated with 50% serum for 1 hr, 3 hrs, and 24 hrs respectively.

The fusion protein and PEGylated protein were incubated with mice serum at a 1:1 ratio at 37° C. for 1 hr, 3 hrs, and overnight. SDS-PAGE was then used to analyze the protein stability. The fusion protein, even after 24 hrs incubation, showed no degradation; however, about 50% percent of PEGylated protein was degraded after 24 hours, but with no degradation after 1 hr and 3 hrs incubation, as shown in FIG. 5. The degradation of PEGylated protein was more likely due to detachment of the PEGylation reagent due to the extended 37° C. incubation, possibly caused by oxidation in non-reduced conditions, than serum protease digestion.

Example 12

Stability of the Fusion Protein

Figure 7:
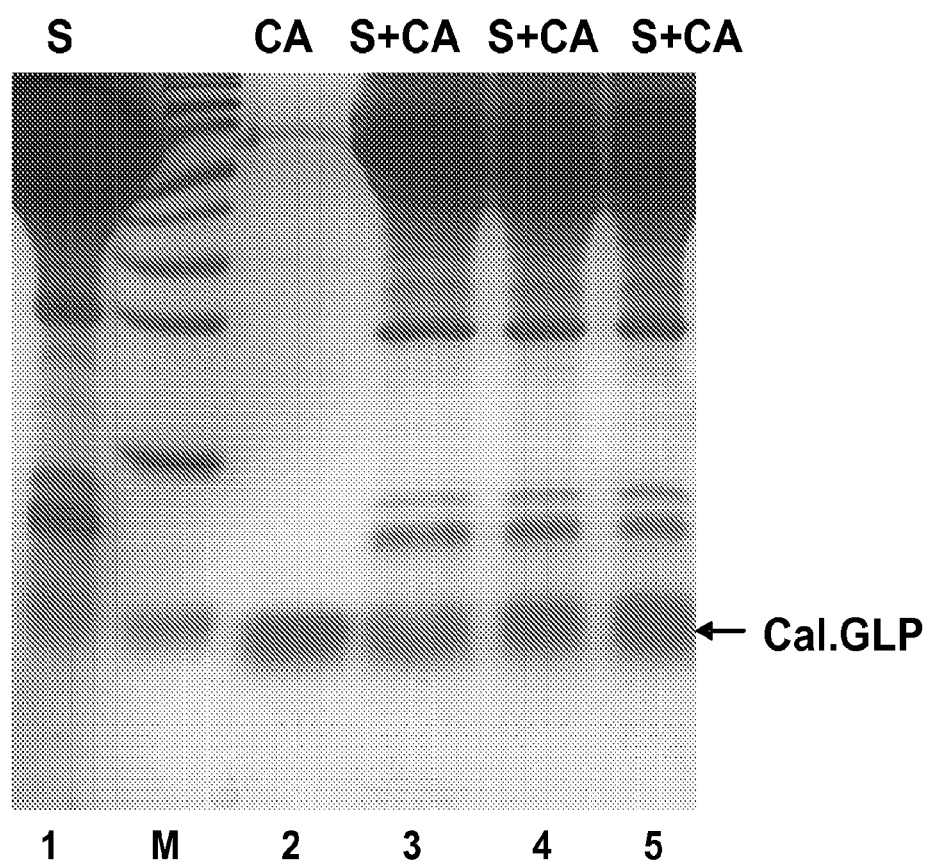
FIG. 7 is a digital image of an SDS-PAGE analysis of serum stability of the fusion protein Cal.GLP. 50 mM Cal-.GLP was incubated with 75% human serum (S+CA) in 25 ml at 37° C. for 1 hour (lane 3), 3 hours (lane 4), and 24 hours (lane 5). The mixture was separated by 16% SDS-PAGE and visualized by coomassie blue staining. Lane 1 is 75% human serum (S) and lane 2 is Cal.GLP only (CA). Lane M is molecular weight markers.
Figure 8:
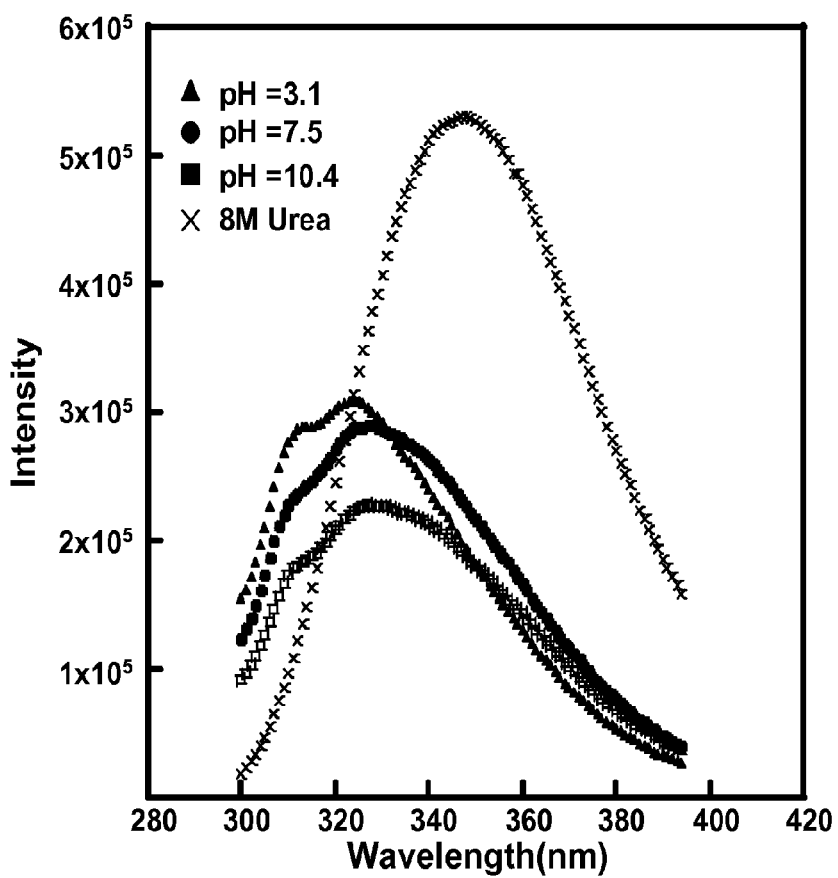
FIG. 8 is a graph showing the fluorescence spectrum of the protein Cal.GLP (50 μM) at various pH values. The spectrum at each pH was compared to that of completely denatured Cal.GLP in 8M Urea.

The fusion protein Cal.GLP was incubated with 75% human serum for a time course (up to 48 hrs). The protein was then analyzed by SDS-PAGE and stained by coomassie blue. It was clear that the protein remained intact after 48 hour incubation with human serum, as shown in FIG. 7. NMR and fluorescence spectrum analyses of the fusion protein in different pH conditions (pH, 3, 5, 7, 9, 10) showed that the protein remained folded in wide ranges of pH conditions (FIG. 8) is the fluorescence spectrum of the protein in pH 3, 7, and 10 as examples), suggesting a strong resistance to pH denaturing.

Example 13

Large Scale Expression and Purification of Fusion Protein from Bacterial *E. coli*

The fusion protein was engineered by replacing C-terminal α-helix of calbindin D9k with the GLP-1 sequence (as shown in FIG. 6). To produce the fusion protein in large quantity, a purification procedure that does not include affinity chromatography was tested.

The protein remained intact and folded after boiling for 10 minutes. This property led to a simplified one ion-exchange column chromatography procedure of protein purification. The bacterial lysate was boiled for 10 minutes. Most bacterial proteins were precipitated due to denaturing by boiling. The fusion protein stayed in supernatant. The protein was then further purified by an ion-exchange column. Approximately 30-50 mg purified fusion protein per liter of bacterial culture were obtained.

Example 14

The Fusion Protein Bound to GLP-R Expression Cells

Figure 10:
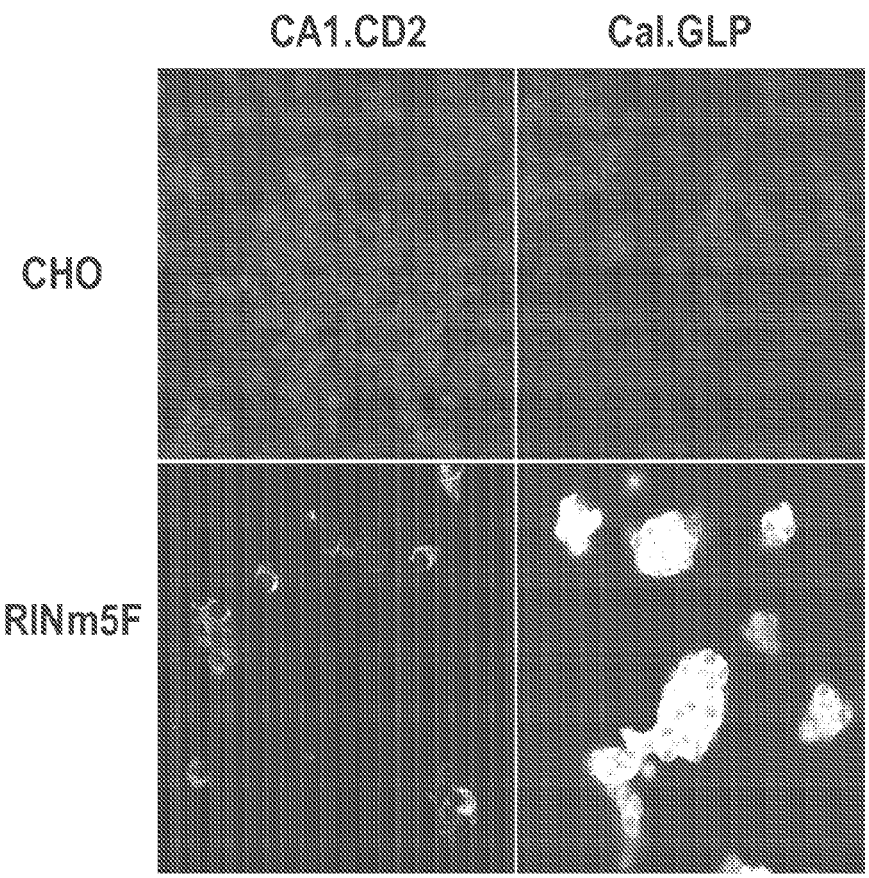
FIG. 10 is a series of digital images showing immunofluorescence staining of CHO or RINm5F cells that were treated by calbindin (50 μM) and Cal.GLP (10 μM). The cells were extensively washed after 30 min treatments under 37° C. in microscopic chamber slides and subsequently fixed. The cells were stained with the calbindin-specific antibody and visualized under confocal microscopy. The light shading represents antibody staining.

To examine whether the developed protein indeed interacted with GLP-1R, the binding of the fusion protein with two cell lines, RINm5F and CHO cells was examined. It is well known that GLP-1R is expressed in RINm5F but not in CHO cells. Both RINm5F and CHO cells were incubated with fusion protein Cal.GLP (10 μM) or calbindin D9k (50 μM) at 37° C. for 30 mins. After extensive washing, the cells were fixed and subjected to immunostaining analyses using a rabbit polyclonal antibody against parental protein calbindin D9k. Cal.GLP bound to RINm5F cells but not CHO cells, while calbindin did not bind to either cell (FIG. 10). The results indicated that the developed protein indeed interacted with GLP-1R in the cell based assay. Similar binding analyses were carried out with RINm5F cells and a pancreatic β-cell line (αTC1). Cal.GLP bound to RINm5F but not to αTC1 cells, indicating that Cal.GLP interacts with β-cells specifically.

Example 15

The Fusion Protein Exhibited High and Lasting Activity in Lowering Blood Glucose in Diabetic Mice The developed protein agent was tested to determine whether it had the in vivo capability of lowering blood glucose in diabetic subjects. Diabetic mice (BKS.Cg-Lepr$^{db/db}$, The Jackson Laboratory) were used as test subjects. A group of six animals first fasted for 6 hours. After fasting, the animals were fed for 30 minutes. The protein agent was administered after feeding by intraperitoneal injection at a dose of 25 nmole/kg. The animals were fed again for 30 mins, 5 hrs after agent administration. Blood samples were taken at different time points after administration of the agent. Glucose concentration in the blood samples was measured using a commercially available kit.

Figure 11:
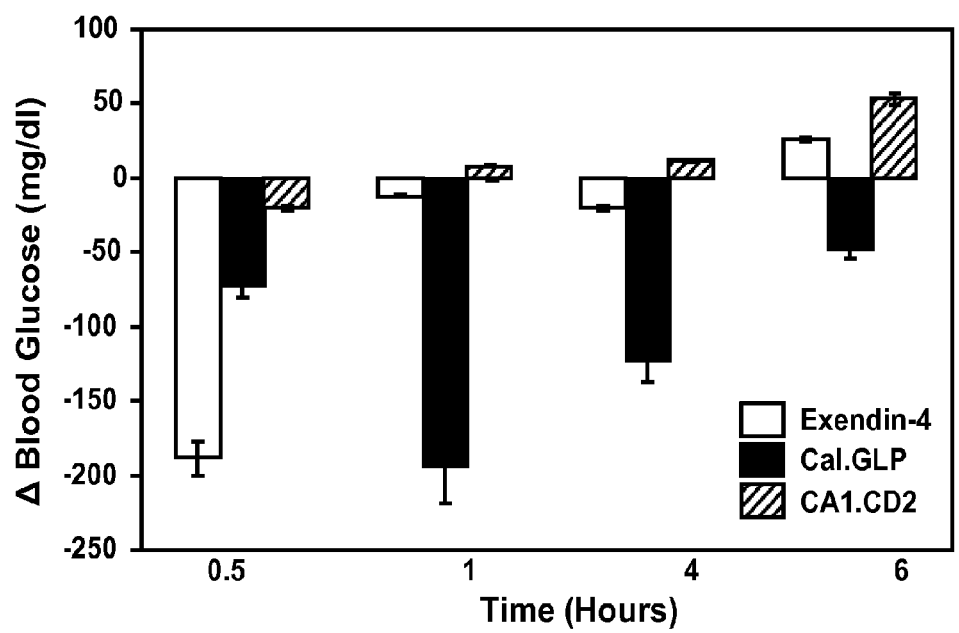
FIG. 11 is a graph showing changes of blood glucose levels (A) in a group of 8 diabetic mice at different time points (indicated) after injection of exendin-4 (open bars), Cal.GLP (filled bars), and calbindin (grey bars) at dose of 25 nmole/kg were measured using a glucose measurement kit. The animals were re-feed for 25 minutes 5 hours after drug administration and 35 minutes before the last time point of blood sample collection. The A Blood Glucose (mg/dl) was determined by calculating the difference between the measured blood glucose levels at any given time point and the initial blood glucose levels. The initial blood glucose levels were measured after feeding for 20 min and before the drug administration (time zero). The error bars represent standard deviations of measurements of eight mice.

It was evident that blood glucose levels dropped about 215 mg/dl in the 4 hour time course. There was a minor increase in blood glucose levels in the animals 6 hours post administration of the agent and one hour after re-feed (FIG. 11). In the control group, the blood glucose levels decreased slightly in the animals that were treated via the parental protein calbindin at the same dose (FIG. 11). As a comparison, the animals were also treated with exendin-4 at the same dose. It was evident that there was a very quick decrease (within 30 minutes) in blood glucose levels (dropped about 189 mg/dl). The blood glucose in the exendin-4 treated animals experienced a significant increase 4 hours post administration of the drug and almost reached the same blood glucose levels before the drug treatments 6 hours and one hour after re-feed (FIG. 11). The experiments indicated that the fusion agent is effective in lowering blood glucose in the diabetic subjects. The treatment with the fusion protein agent led to a bigger blood glucose decrease and significantly longer effective time compared to that of exendin-4.

Example 16

The Fusion Protein is Effective in Lowering Blood Glucose and Stimulating Glucose-Dependent Insulin Secretion The effects of the developed agent on blood glucose lowering and stimulating of the glucose-dependent insulin secretion in diabetic mice were also examined. The animals first fasted for 6 hours. The protein agent (25 nmole/kg) and glucose (15 mmole/kg) were co-administrated via intraperitoneal injection with a group of eight diabetic mice. The blood glucose and insulin levels were measured at different time points. As controls, the same dose of glucose was administrated alone and co-administrated with the parental protein calbindin in separate groups of diabetic mice. As a comparison, the same tests were also carried out with the same dose of exendin-4.

Administration of both exendin-4 and the developed protein agent led to dramatic blood glucose lowering post glucose and the drug administrations in the diabetic mice, while the administration of the parental protein did not. As observed in the above test, administration of the protein agent resulted in larger glucose lowering in longer duration compared to that of the treatment with exendin-4 (FIG. 12).

Figure 12:
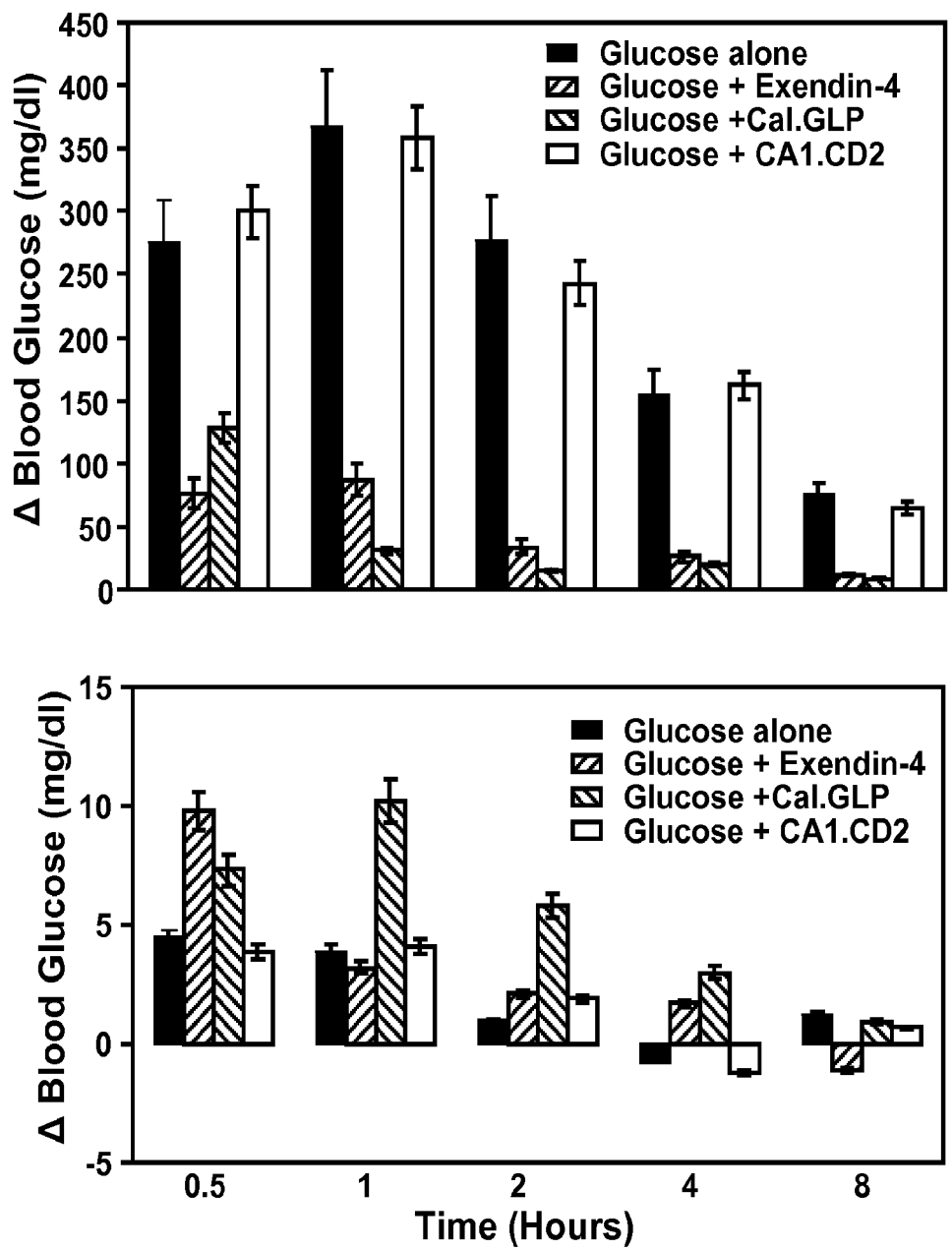
FIG. 12 is a pair of graphs showing the changes in Δ blood glucose (Upper panel) and Δ insulin (bottom panel) in a group of 8 diabetic mice at different time points after injection of 15 mmole/kg of glucose with 25 nmole/kg of different agents.

An immediate insulin increase and glucose decrease were observed (within 30 mins.) with exendin-4 treatment, while the effects of increase in insulin and decrease in glucose lasted almost 2 hrs with the mice treated with the developed protein agent (FIG. 12).

Example 17

The Engineered Protein is Effective in Lowering Blood Glucose

The effects of the developed agent and PEGylated agents on blood glucose lowering in diabetic mice were examined. The animals were fast for 6 hours. Following the fasting, the animals were feed for 30 minutes and immediately followed by a blood draw. Agent (indicated in the figures at 25 nmole/kg) were administrated by i.p. The animals were then returned to the cages. Blood samples (~20 µl) was draw at 30, 120, 240 minutes after agent administration. Glucose in blood samples was measured.

Figure 17:
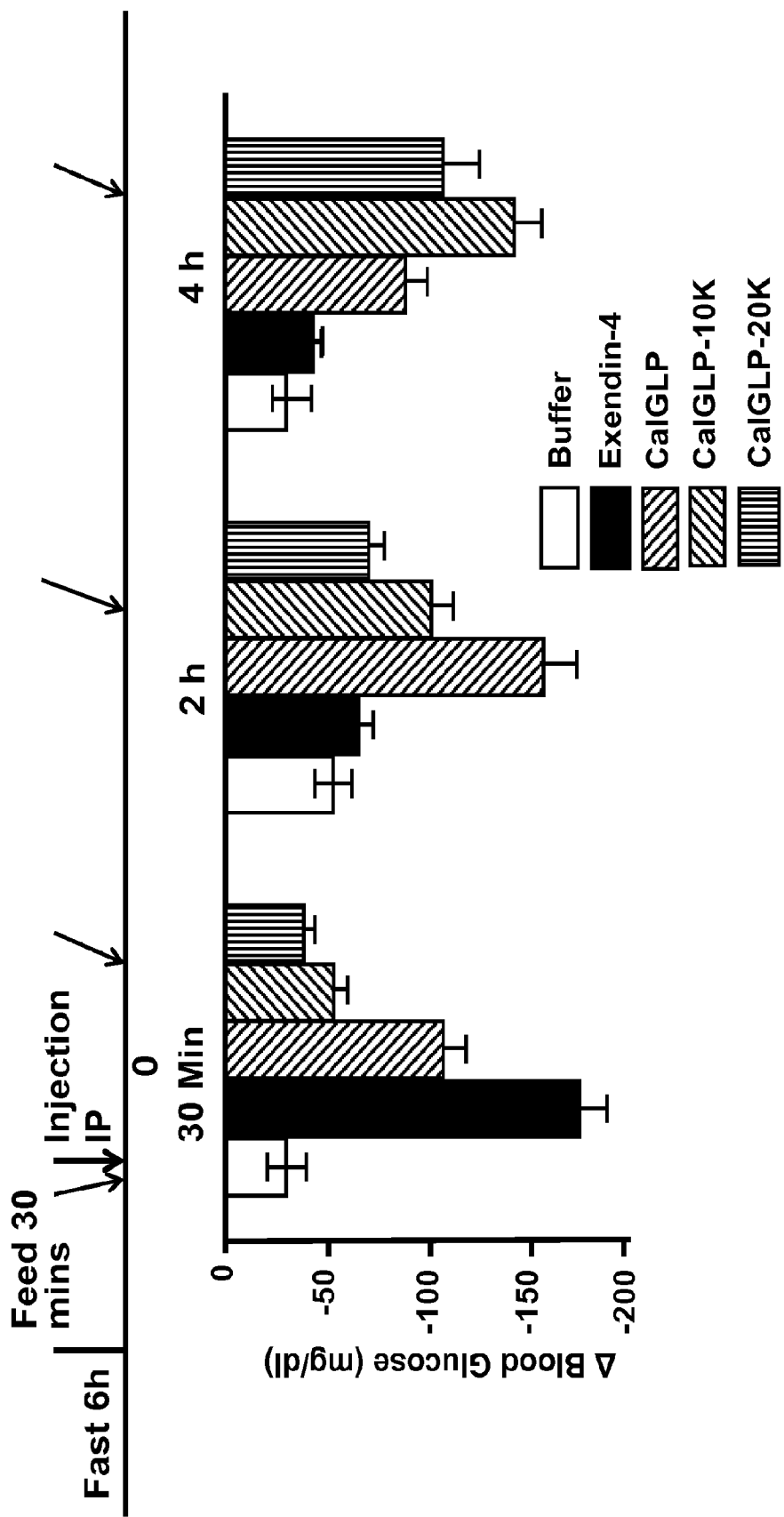
FIG. 17 is a graph showing the effects of Buffer, Exendin-4, CalGLP, and CalGLP-10K on blood glucose. The animals were fast for 6 hours. Following the fasting, the animals were feed for 30 minutes and immediately followed by a blood draw. Agent (indicated in the figures at 25 nmole/kg) were administrated by i.p. The animals were then returned to the cages. Blood samples (about 20 ml) was draw at 30, 120, 240 minutes after agent administration. Glucose in blood samples was measured. Δblood glucose are the differences of blood glucose draw at the time points of purple arrows and red arrow.

Administration of both PEGylated and unPEGylated proteins led to dramatic blood glucose lowering in the diabetic mice. The PEGylated proteins exhibited a delayed effect (FIG. 17.

Example 18

The PEGylated Engineered Protein Had a Long Lasting Effective in Lowering Blood Glucose The effects of the developed agent and PEGylated agents on blood glucose lowering in diabetic mice were examined in a long time course. Agent (indicated in the figures at 25 nmole/kg) were administrated by i.p. at time zero. The animals were fast for 6 hours. Following the fasting, blood samples (~20 µl) was draw immediately following fasting. The animals were then feed for 30 minutes and immediately followed by a blood draw. The animals were then returned to the cages. The same procedures were repeated at indicated time points. Glucose in blood samples was measured.

Figure 18:
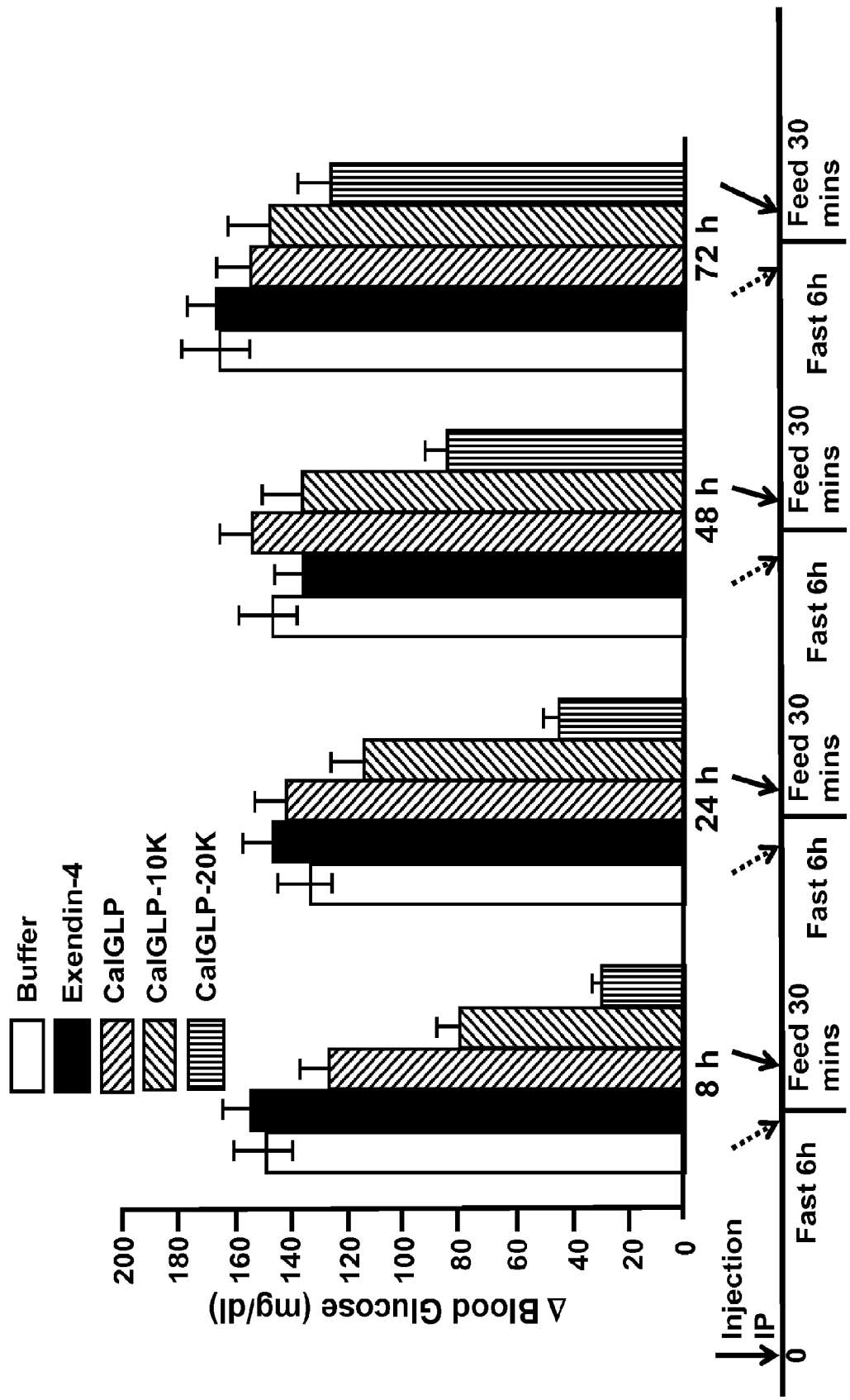
FIG. 18 shows the difference in blood glucose levels between after refeeding and after fasting/before refeeding at the indicated time points. The agents (25 nmole/kg) were administrated (i.p) at time zero. Agent (indicated in the figures 25 nmole/kg) were administrated by i.p. at time zero. The animals were fast for 6 hours. Following the fasting, blood samples (about 20 ml) was draw immediately following fasting. The animals were then feed for 30 minutes and immediately followed by a blood draw. The animals were then returned to the cages. The same procedures were repeated at indicated time points. Glucose in blood samples was measured. Δblood glucose are the differences of blood glucose draw at the time points of purple arrows and corresponding red arrows.

The effect of administration of one dose of 20 kDa PEGylated protein lasted for at least 24 hour in diabetic mice, while the effect of administration of one dose of 10 kDa PEGylated protein lasted about 7-9 hours in diabetic mice (FIG. 18).

Example 19

The Engineered Protein Had Long Term Effect in Lowering Blood Glucose

The effects of the developed agent and PEGylated agents on blood glucose lowering in diabetic mice were examined in a four week treatment course. Agents (indicated in the figures at 25 nmole/kg) were administrated by i.p. daily at the same time 2:00 pm for 4 weeks. The animals were returned to the ages. Blood samples (~20 µl) were draw daily at 5:00 pm for 4 weeks. Glucose in blood samples was measured. Blood glucose levels were plotted against day. Animal body weight was weighed daily before drawing blood. Average body weight of each group of six mice was plotted against days.

Figure 19:
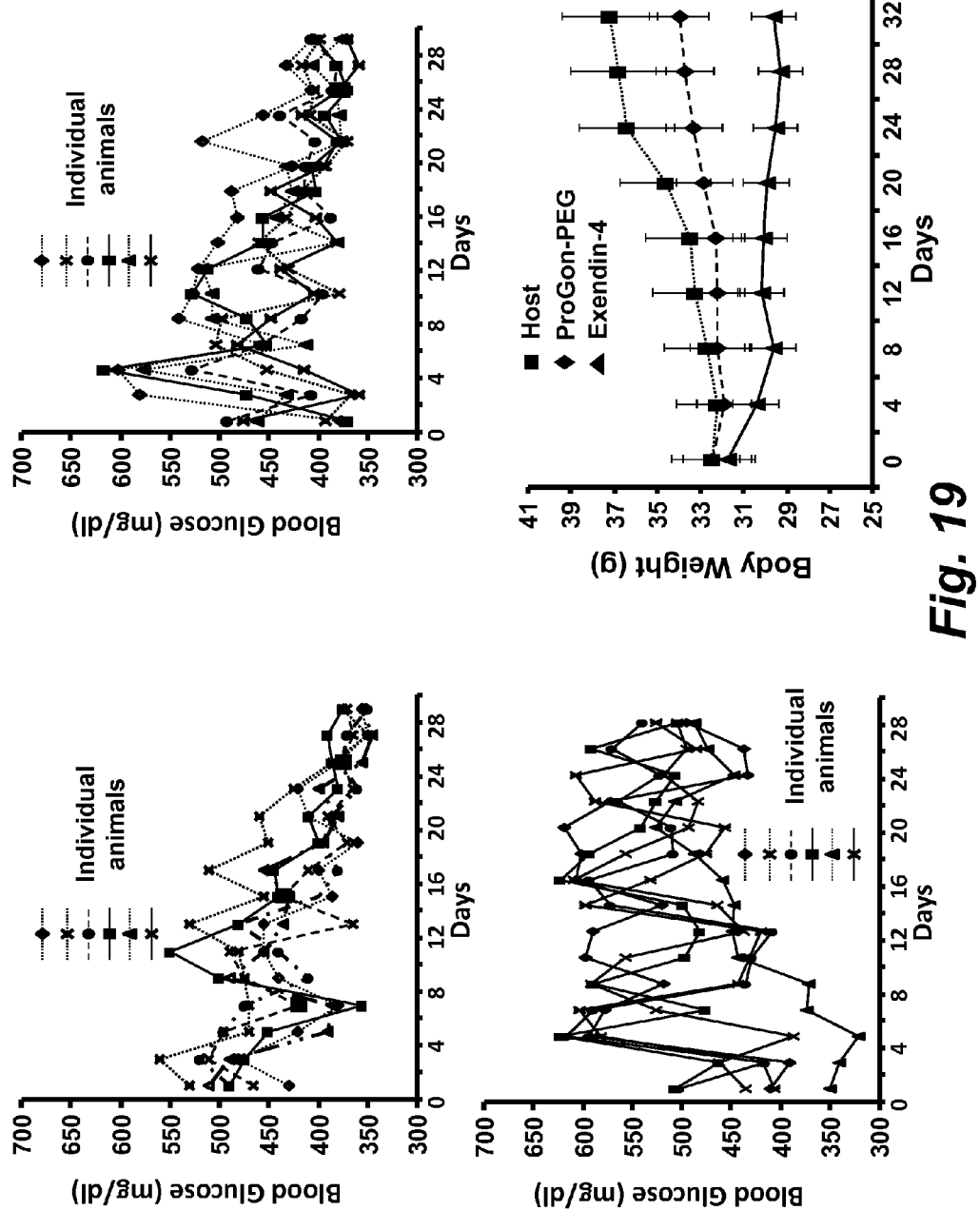
FIG. 19 shows a series of graphs illustrating blood glucose measured daily at 5:00 pm every day. Agents (indicated in the figures 25 nmole/kg) were administrated by i.p. at daily at the same time 2:00 pm for 4 weeks. The animals were returned to the ages. Blood samples (about 20 ml) were draw daily at 5:00 pm for 4 weeks. Glucose in blood samples was measured. Blood glucose levels were plotted against day. Animal body weight was weighed daily before drawing blood. Average body weight of each group of six mice was plotted against days.

Administration of the agent daily led to lowering and stabilizing the blood glucose levels in diabetic mice. The developed agent showed stronger effects in lowering and stabilizing the blood glucose. Unlike the treatment with exendin-4, treatment with the developed agent did not result significant weight gain or lose (FIG. 19).

Example 20

Fusion Protein Bound to $Gd^{3+}$ and Exhibited High R1 and R2 Relaxivity

To ensure that the fusion protein is applicable as a MRI contrast agent, the $Gd^{3+}$ binding property and R1/R2 relaxivity of the fusion protein were tested using well-known methods. The metal binding analyses indicated that the Cal.GLP had $Gd^{3+}$ binding ability and metal selectivity similar to those of the parental protein calbindin (Table 1). Measurement of R1 and R2 relaxivity of the Gd-Cal.GLP and Gd-calbindin at 1.4 T using a relaxometer revealed that the Gd-Cal.GLP had slightly higher R1 and R2 relaxivity than that of calbindin (Table 2). $Gd^{3+}$ binding analyses and relaxivity measurements indicated that the developed protein Cal.GLP can be used as a MRI contrast agent with high contrast-enhancing capability.

TABLE 2

The metal binding affinities and relaxivity of fusion proteins

| | LgKa $Gd^{3+}$ | LgKa $Ca^{2+}$ | R1 $mM^{-1}S^{-1}$ | R2 $mM^{-1}S^{-1}$ |
|---|---|---|---|---|
| calbindin | 12.6 | <2.3 | 6.58 | 9.07 |
| Cal.GLP/Q26D | 13.5 | <2.1 | 20 | 30 |
| DTPA | 22.5 | 10.8 | 3.8 | 7.1 |

Example 21

Toxicity of the Protein Agent

Toxicity of the parental protein CA1.CD2 was previously analyzed, and was not toxic in mice. To ensure that the new design (addition of GLP-1 and conjugation of Cy5.5) does not cause alteration of toxicity of the agent, the toxicity of the GLP-1R target protein agent was re-examined using healthy CD-1 mice. One group of mice (7 mice per group) were injected with one dose of 100 µl of the agent (6 mM) and another group of animals were injected with two doses of the agent (100 µl of agent (6 mM)) with 8 hours time interval between the two injections. The animals were returned to their cages for 14 days. Among 14 tested mice, no mouse died. All animals behaved normally (no change in eating habits. No abnormal weight gain or loss. No abnormal appearance on fur). The fusion protein agent did not have acute toxicity at the injected doses (almost double the dose used in the MRI experiments).

Example 22

Immunogenicity

Figure 15:
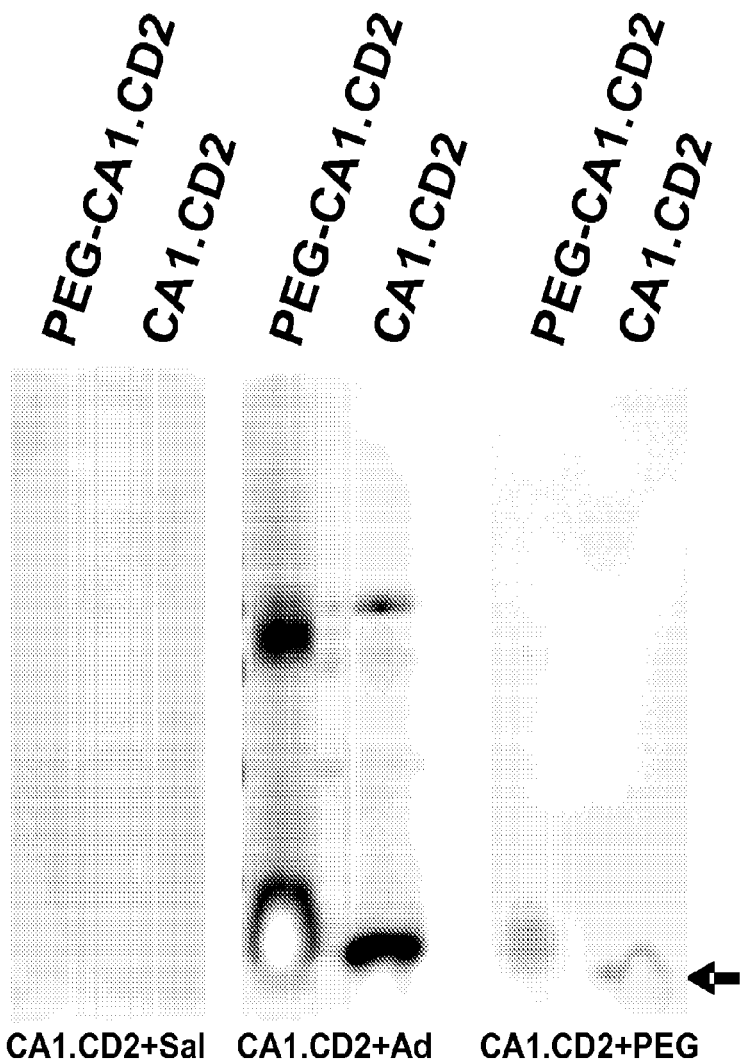
FIG. 15 is a series of digital images showing Western blot analyses of antibody produced in rabbits serum after intraperitoneal injection of protein CA1.CD2 or PEGylated CA1.CD2 (CA1.CD2+PEG). Western blots were performed with anti-serum (3rd bleed) from rabbits that were injected as follows; CA1.CD2 mixed with buffered saline (left panel, CA1.CD2+Sal), CA1.CD2 mixed with adjuvant (middle panel, CA1.CD2+Ad); PEGylated CA1.CD2 (right panel, CA1.CD2+PEG). The Western blots experiments were carried out with 0.5 μg of PEGylated (PEG-CA1.CD2) or unmodified CA1.CD2 (CA1.CD2). Arrow indicates the position of the detected protein bands.

The immunoresponse of the parental protein CA1.CD2 (without addition of GLP-1) was characterized in rabbits. The PEGylated (PEG-40) and un-PEGylated CA1.CD2 were injected into rabbits with/without adjuvant followed by repeating the injection three times. Serum samples from the injected rabbits were collected 7 days after each injection. The antibodies in the rabbit serum samples were then analyzed by immunoblot of the antigen proteins using the serum (FIG. 15). No significant immunoresponses were observed without mixing the antigen with adjuvant. PEGylation of the protein further greatly reduced the antibody production in the rabbits against the both PEGylated and unPEGylated CA1.CD2. There was quite weak antibody production only after four unPEGylated antigen injections. The fusion protein agent does not generate strong immunoresponse in rabbits.

Example 23

To Image Pancreatic β-Cells by Targeting GLP-1R Using the Developed Protein Agent We have created a protein agent that binds GLP-1R specifically. The protein carries a rationally fusion high affinity $Gd^{3+}$ binding site. Our analyses demonstrated that the developed protein agent exhibited very high R1 and R2 relaxivity providing a potential as an effective GLP-1R targeting MRI contrast agent. A similar host protein that carries HER2 targeting moiety had been successfully used in molecular MR imaging by targeting cancer marker HER2. Thus, we reasoned that we should be able to use our created GLP-1R targeting protein for MR imaging of pancreatic β-cells by targeting GLP-1R. The ability of beta cell imaging is critical in developing therapeutics for diabetes, especially cell and islet based treatments. The imaging tools, especially the MR imaging tool, that allow β-cells imaging are currently not available.

We performed the imaging studies with CD-1 mice using our developed protein Gd-Cal.GLP/Q26D variant as the contrast agent. The in vivo imaging experiments tested whether our developed agent can image mouse pancreas by targeting GLP-1R.

Figure 20:
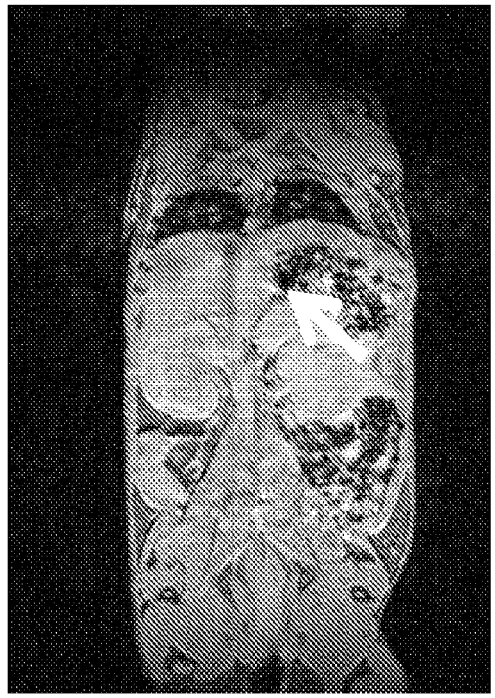
FIG. 20 shows a series of digital images showing the results of CD1 mice injected (i.v.) 80 ml of Gd-CalGLP (5 mM). The arrows indicate the pancreas.
Figure 20:
Figure 20:
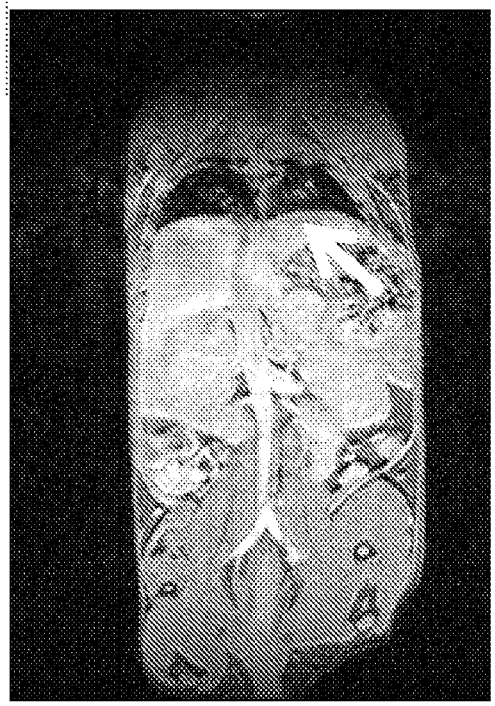
Figure 20:
Figure 21:
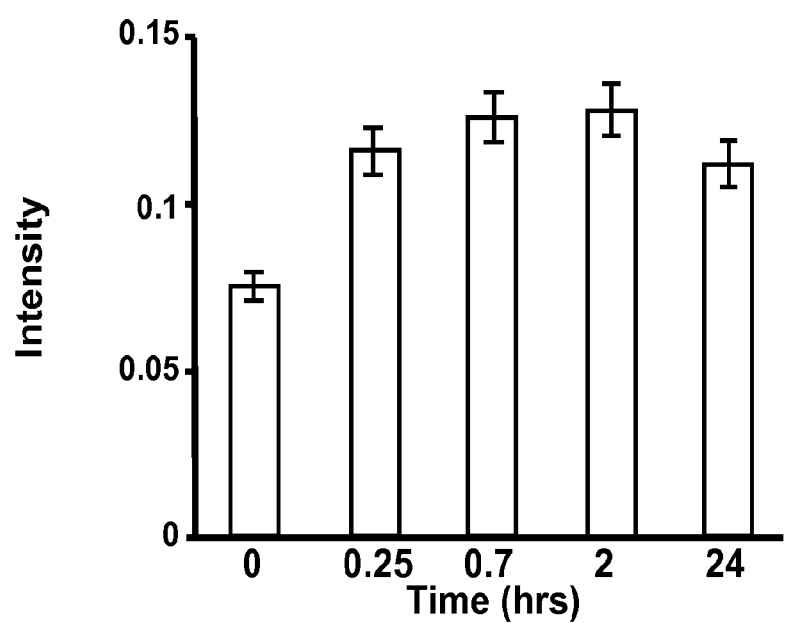
FIG. 21 shows a graph showing MR image intensities at the pancreas measured at different time points after administration of Gd-CalGLP. Error bars are standard deviations of measurements of 8 different ROIs.

The same MR imaging procedures as described in our previous studies was employed here to image CD-1 mice (Yang et al., (2008) *J. Am. Chem. Soc.* 130: 9260-9267). We imaged six mice per group with approximately the same age and weight. The animals were injected (i.v. tail vein) 80 µl of Gd-Cal.GLP/Q26D variant (5 mM). MR imagings were recorded at indicated time after administration of the Gd-Cal.GLP/Q26D. All MRI scans will be carried out using a Varian Unity 4.7 T MR scanner with a specially made mouse coil. During MR scan, the mouse was under anesthesia with 1.5% isoflurane and kept warm with a heated pad. MR images were acquired by either T1- and T2-weighted fast spin echo sequences (TR=2 s, TE=0.022 s, and ESP=0.01 s with field of view of 3×3 cm, matrix of 256×256, and slice thickness of 1 mm) or 3D gradient echo sequence (TR=0.04 s, TE=0.029 s, with field of view of 8×4×2.8 cm, matrix of 384×192×64). MR image intensities at the pancreas were measured at different time points (indicated in the figure) after administration of Gd-Cal.GLP/Q26D. It was clear that administration of the contrast agent led to strong contrast enhancements at pancreas (FIGS. 20 and 21). MR image intensities at the pancreas were measured at different time points (indicated in FIG. 21) after administration of Gd-CalGLP. The intensities were normalized to the background intensity. Error bars are standard deviations of measurements of 8 different ROIs.

Figure 22A:
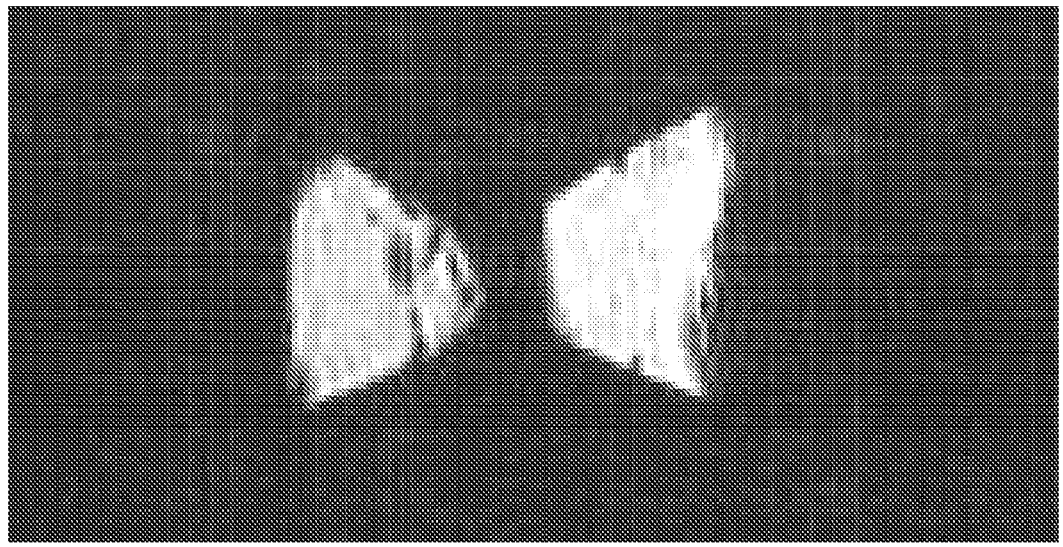
FIG. 22A is a series of digital images showing pancreases from CD1 mice that were harvested 24 hours after injection of 80 ml of Gd-CalGLP (5 mM) (Gd-CalGLP) or 80 ml of buffer saline (No Gd-CalGLP).
Figure 22B:
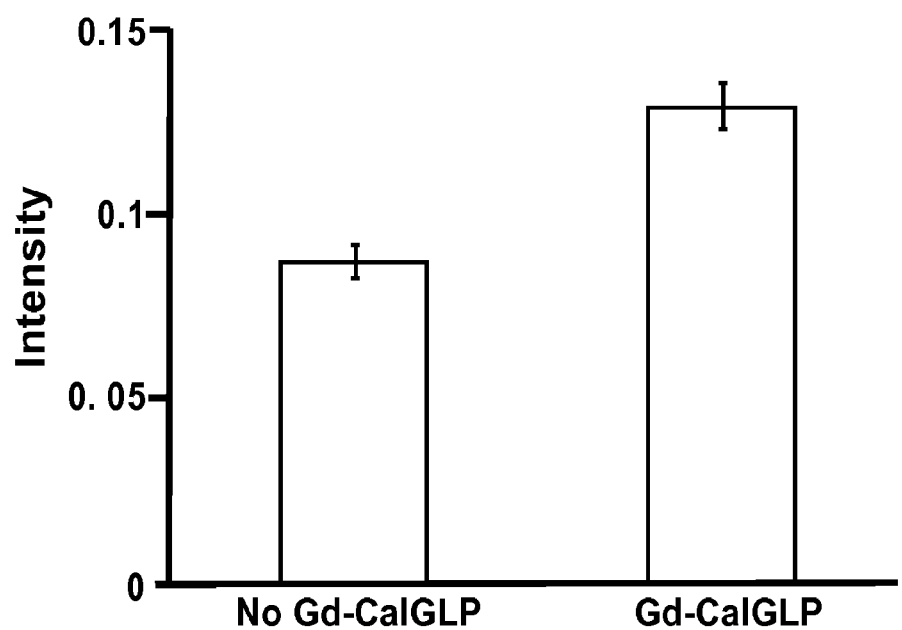
FIG. 22B is a graph showing intensities of the images of FIG. 22A normalized to the background intensity. Error bars are standard deviations of measurements of 8 different ROIs.

To further prove the MRI contrast enhancement at pancreas, Mice pancreases were collected in 1.5 ml tubes 24 hours post injection of the contrast agent or buffer saline. The collected pancreases were scanned by fast spin echo and gradient echo sequence with same parameters as in MR imaging of mice. Clearly, there was a strong contrast enhancement with the pancreas from mouse that was administrated the contrast agent compared to that of pancreas from mouse that was administrated buffer saline (FIGS. 22A and B). The intensities were normalized to the background intensity. Error bars are standard deviations of measurements of 8 different ROIs.

Example 24

Figure 13:
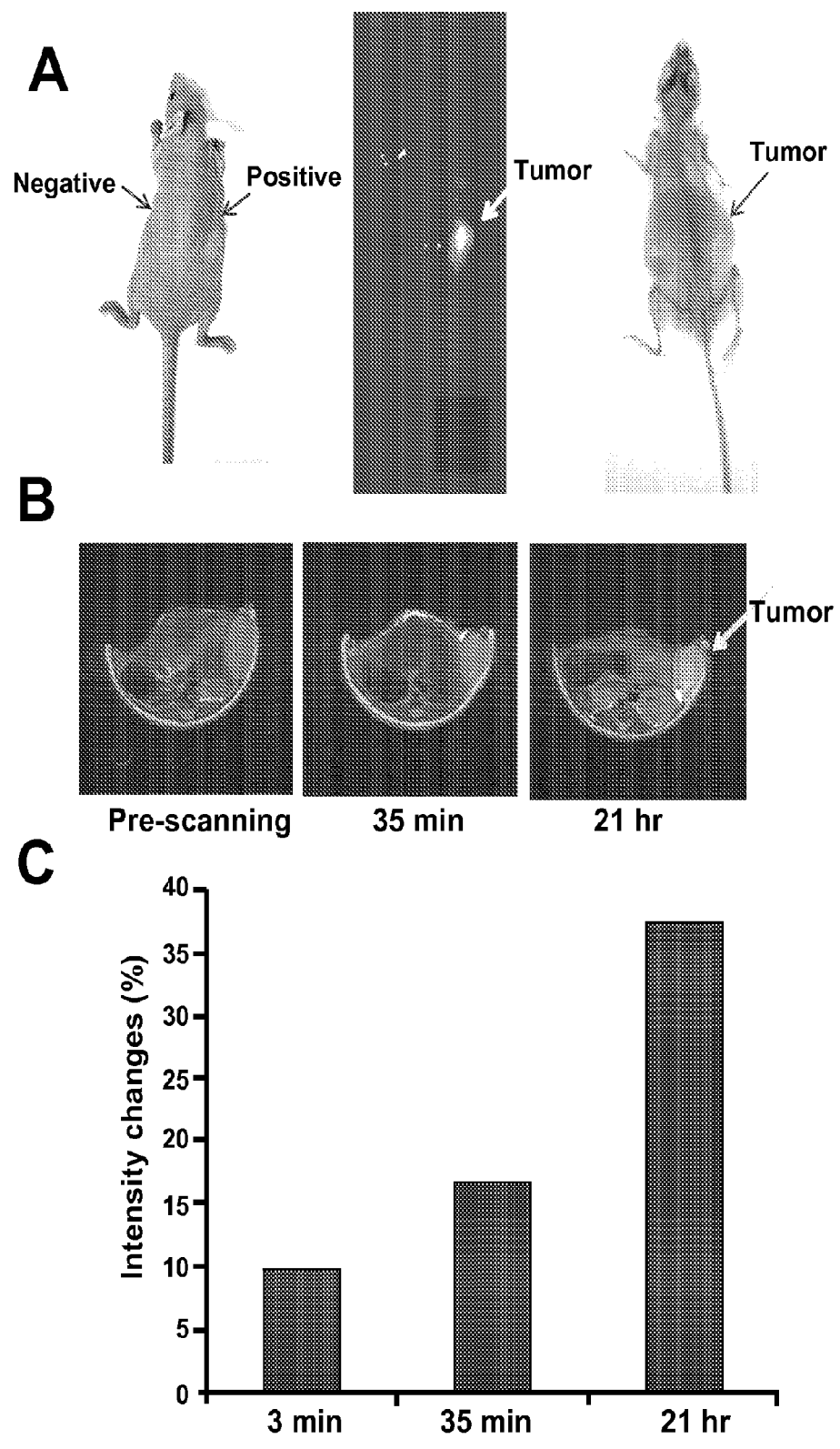
FIG. 13A is a series of digital images showing nude mice inoculated with negative cell line MDA-MB-231 and positive cell line SKOV-3. The cell number for each spot was about 5×10$^6$. The specific binding of positive tumor on the right upon injection of the dual-labeled contrast Gd-CA1-Affi-Cy5.5 was visualized using Kodak NIR in vivo FX-pro animal imaging system 21 hours poster injection.
FIG. 13B shows digital traverse MR images of tumor mice at 4.7 T with fast spin echo obtained before, and 35 mins., and 21 hrs following administration of the contrast agent.
FIG. 13C is a graph showing the intensity enhancement at the positive tumor by an embodiment of the contrast agent of the disclosure analyzed by Image J.

FIG. 13A is a series of digital images showing nude mice inoculated with negative cell line MDA-MB-231 and positive cell line SKOV-3. The cell number for each spot was about $5 \times 10^6$. The specific binding of positive tumor on the right upon injection of the dual-labeled contrast Gd-CA1-Affi-Cy5.5 was visualized using Kodak NIR in vivo FX-pro animal imaging system 21 hours poster injection.

FIG. 13B shows digital traverse MR images of tumor mice at 4.7 T with fast spin echo obtained before, and 35 mins., and 21 hrs following administration of the contrast agent.

FIG. 13C is a graph showing the intensity enhancement at the positive tumor by an embodiment of the contrast agent of the disclosure analyzed by Image J.

Figure 14:
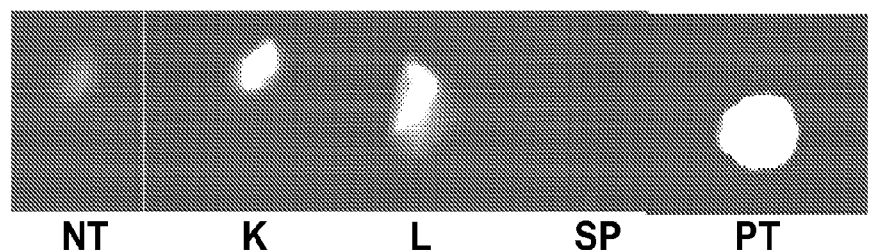
FIG. 14 is digital images showing NIR imaging of tissues from different organs after MRI imaging of the tumor bearing mice. NT, Negative tumor; K, Kidney; L, Liver; SP, Spleen; PT, Positive tumor.

FIG. 14 is digital images showing NIR imaging of tissues from different organs after MRI imaging of the tumor bearing mice. NT, Negative tumor; K, Kidney; L, Liver; SP, Spleen; PT, Positive tumor.

What is claimed:

1. A fusion protein comprising a first peptide, wherein the first peptide is glucagon-like peptide-1 (GLP-1), glucagon-like peptide-1 (GLP-1) (7-36), or glucagon-like peptide-1 (GLP-1) (9-36) linked to a second peptide, wherein the second peptide is a region of calbindin D9k, and wherein the fusion protein is more stable than the first peptide alone, the second peptide having an amino acid sequence selected from the group consisting of: MSTKKSPEELKRIFEKYAAKEGDPDQLSKDELKLLIQAEFPSLLKGPNTLDDLFQELDKNG (SEQ ID NO: 2), MSTKKSPEELKRIFEKYAAKEGDPDQLSKDELKLLIQAEFPCLLKGPNTLDDLFQELDKNG (SEQ ID NO: 3), MSTKKSPCELKRIFEKYAAKEGDPDQLSKDELKLLIQAEFPSLLKGPNTLDDLFQELDKNG (SEQ ID NO: 4), and MSTKKSPEELKRIFEKYAAKEGDPDDLSKDELKLLIQAEFPCLLKGPNTLDDLFQELDKNG (SEQ ID NO: 17).

2. The fusion protein of claim 1, further comprising a detectable label attached thereto.

3. The fusion protein of claim 1, wherein the fusion protein further comprises at least one polyethylene glycol compound conjugated thereto.

4. A fusion protein comprising a first peptide having the amino acid sequence HAEGTFTSDVSSYLEGQAAKEFIAWLVKGR (SEQ ID NO: 1) and linked to a second peptide having the amino acid sequence MSTKKSPEELKRIFEKYAAKEGDPDQLSKDELKLLIQAEFPSLLKGPNTLDDLFQELDKNG (SEQ ID NO: 2), and wherein the fusion protein is more stable than the first peptide alone.

5. A method of regulating glucose metabolism in an animal or human cell, comprising: administering to an animal or human cell a pharmaceutically acceptable composition comprising a fusion protein comprising a first peptide, wherein the first peptide is glucagon-like peptide-1 (GLP-1), glucagon-like peptide-1 (GLP-1) (7-36), or glucagon-like peptide-1 (GLP-1) (9-36) linked to a second peptide, wherein the second peptide is a region of calbindin D9k, and wherein the fusion protein is more stable than the first peptide alone, the second peptide having an amino acid sequence selected from the group consisting of: MSTKKSPEELKRIFEKYAAKEGDPDQLSKDELKLLIQAEFPSLLKGPNTLDDLFQELDKNG (SEQ ID NO: 2), MSTKKSPEELKRIFEKYAAKEGDPDQLSKDELKLLIQAEFPCLLKGPNTLDDLFQELDKNG (SEQ ID NO: 3), MSTKKSPCELKRIFEKYAAKEGDPDQLSKDELKLLIQAEFPSLLKGPNTLDDLFQELDKNG (SEQ ID NO: 4), and MSTKKSPEELKRIFEKYAAKEGDPDDLSKDELKLLIQAEFPCLLKGPNTLDDLFQELDKNG (SEQ ID NO: 17); and whereby the fusion protein selectively binds to a GLP-1 receptor of the cell, thereby regulating the activity of the receptor and glucose metabolism by the cell.

6. The method of claim 5, wherein the first peptide has the amino acid sequence HAEGTFTSDVSSYLEGQAAKEFIAWLVKGR (SEQ ID NO: 1), and the second peptide has an amino acid sequence selected from the group consisting of: MSTKKSPEELKRIFEKYAAKEGDPDQLSKDELKLLIQAEFPSLLKGPNTLDDLFQELDKNG (SEQ ID NO: 2), MSTKKSPEELKRIFEKYAAKEGDPDQLSKDELKLLIQAEFPCLLKGPNTLDDLFQELDKNG (SEQ ID NO: 3), MSTKKSPCELKRIFEKYAAKEGDPDQLSKDELKLLIQAEFPSLLKGPNTLDDLFQELDKNG (SEQ ID NO: 4), MSTKKSPEELKRIFEKYAAKEGDPDDLSKDELKLLIQAEFPCLLKGPNTLDDLFQELDKNG (SEQ ID NO: 17).

7. A method of enhancing imaging contrast, comprising:
(i) delivering to a target cell a pharmaceutically acceptable imaging probe composition comprising a fusion probe, wherein the fusion probe comprises:
a fusion protein comprising a first peptide, wherein the first peptide is glucagon-like peptide-1 (GLP-1), glucagon-like peptide-1 (GLP-1) (7-36), or glucagon-like peptide-1 (GLP-1) (9-36) linked to a second peptide, wherein the second peptide is a region of calbindin D9k, and wherein the fusion protein is more stable than the first peptide alone, the second peptide having an amino acid sequence selected from the group consisting of: MSTKKSPEELKRIFEKYAAKEGDPDQLSKDELKLLIQAEFPSLLKGPNTLDDLFQELDKNG (SEQ ID NO: 2), MSTKKSPEELKRIFEKYAAKEGDPDQLSKDELKLLIQAEFPCLLKGPNTLDDLFQELDKNG (SEQ ID NO: 3), MSTKKSPCELKRIFEKYAAKEGDPDQLSKDELKLLIQAEFPSLLKGPNTLDDLFQELDKNG (SEQ ID NO: 4), and MSTKKSPEELKRIFEKYAAKEGDPDDLSKDELKLLIQAEFPCLLKGPNTLDDLFQELDKNG (SEQ ID NO: 17); and
a detectable label; and
(ii) detecting a signal from the label, thereby determining the presence of the site of fusion protein binding of the target cell.

8. The method of claim 7, wherein the first peptide of the fusion protein is glucagon-like peptide-1 (GLP-1) (9-36) and the second peptide having an amino acid sequence selected from the croup consisting of: MSTKKSPEELKRIFEKYAAKEGDPDQLSKDELKLLIQAEFPSLLKGPNTLDDLFQELDKNG (SEQ ID NO: 2), MSTKKSPEELKRIFEKYAAKEGDPDQLSKDELKLLIQAEFPCLLKGPNTLDDLFQELDKNG (SEQ ID NO: 3), MSTKKSPCELKRIFEKYAAKEGDPDQLSKDELKLLIQAEFPSLLKGPNTLDDLFQELDKNG (SEQ ID NO: 4), and MSTKKSPEELKRIFEKYAAKEGDPDDLSKDELKLLIQAEFPCLLKGPNTLDDLFQELDKNG (SEQ ID NO: 17).

9. The method of claim 7, wherein the first peptide has the amino acid sequence HAEGTFTSDVSSYLEGQAAKEFIAWLVKGR (SEQ ID NO: 1), and the second peptide has an amino acid sequence selected from the group consisting of: MSTKKSPEELKRIFEKYAAKEGDPDQLSKDELKLLIQAEFPSLLKGPNTLDDLFQELDKNG (SEQ ID NO: 2), MSTKKSPEELKRIFEKYAAKEGDPDQLSKDELKLLIQAEFPCLLKGPNTLDDLFQELDKNG (SEQ ID NO: 3), MSTKKSPCELKRIFEKYAAKEGDPDQLSKDELKLLIQAEFPSLLKGPNTLDDLFQELDKNG (SEQ ID NO: 4), MSTKKSPEELKRIFEKYAAKEGDPDDLSKDELKLLIQAEFPCLLKGPNTLDDLFQELDKNG (SEQ ID NO: 17).

10. The method of claim 7, wherein the first peptide of the fusion protein has the amino acid sequence HAEGTFTSDVSSYLEGQAAKEFIAWLVKGR (SEQ ID NO: 1), the second peptide has an amino acid sequence MSTKKSPEELKRIFEKYAAKEGDPDQLSKDELKLLIQAEFPSLLKGPNTLDDLFQELDKNG (SEQ ID NO: 2), and the label is gadolinium ($Gd^{3+}$), whereby the label is detectable by magnetic resonance imaging (MRI), and wherein the fusion protein binding site is a GLP-1 receptor of a cell of the pancreas.

11. A fusion protein comprising a first peptide, wherein the first peptide of the fusion protein has the amino acid sequence HAEGTFTSDVSSYLEGQAAKEFIAWLVKGR (SEQ ID NO: 1), and linked to a second peptide having the amino acid sequence MSTKKSPEELKRIFEKYAAKEGDPDQLSKDELKLLIQAEFPCLLKGPNTLDDLFQELDKNG (SEQ ID NO: 3), and wherein the fusion protein has the amino acid sequence according to (SEQ ID NO: 15).

12. The fusion protein of claim 2, wherein the detectable label is a gadolinium ($Gd^{3+}$) ion detectable by magnetic resonance imaging.

* * * * *

UNITED STATES PATENT AND TRADEMARK OFFICE
CERTIFICATE OF CORRECTION

PATENT NO.         : 8,697,648 B2
APPLICATION NO.    : 13/503194
DATED              : April 15, 2014
INVENTOR(S)        : Liu et al.

It is certified that error appears in the above-identified patent and that said Letters Patent is hereby corrected as shown below:

In the Specification

Column 1, line 14 please insert the following paragraph after the "Cross Reference to Related Application" paragraph:

--FEDERAL SPONSORSHIP
    This invention was made with Government support under Contract Nos. CA 118113 and CA 127190 awarded by the National Institutes of Health. The Government has certain rights in this invention.--

Signed and Sealed this
Twenty-fourth Day of March, 2015

Michelle K. Lee
*Director of the United States Patent and Trademark Office*

SEQUENCE LISTING

```
<160> NUMBER OF SEQ ID NOS: 18

<210> SEQ ID NO 1
<211> LENGTH: 30
<212> TYPE: PRT
<213> ORGANISM: Artificial sequence
<220> FEATURE:
<223> OTHER INFORMATION: Synthetic peptide

<400> SEQUENCE: 1

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30

<210> SEQ ID NO 2
<211> LENGTH: 61
<212> TYPE: PRT
```

```
<213> ORGANISM: Artificial sequence
<220> FEATURE:
<223> OTHER INFORMATION: Synthetic peptide

<400> SEQUENCE: 2

Met Ser Thr Lys Lys Ser Pro Glu Glu Leu Lys Arg Ile Phe Glu Lys
1               5                   10                  15

Tyr Ala Ala Lys Glu Gly Asp Pro Asp Gln Leu Ser Lys Asp Glu Leu
                20                  25                  30

Lys Leu Leu Ile Gln Ala Glu Phe Pro Ser Leu Leu Lys Gly Pro Asn
            35                  40                  45

Thr Leu Asp Asp Leu Phe Gln Glu Leu Asp Lys Asn Gly
    50                  55                  60

<210> SEQ ID NO 3
<211> LENGTH: 61
<212> TYPE: PRT
<213> ORGANISM: Artificial sequence
<220> FEATURE:
<223> OTHER INFORMATION: Synthetic peptide

<400> SEQUENCE: 3

Met Ser Thr Lys Lys Ser Pro Glu Glu Leu Lys Arg Ile Phe Glu Lys
1               5                   10                  15

Tyr Ala Ala Lys Glu Gly Asp Pro Asp Gln Leu Ser Lys Asp Glu Leu
                20                  25                  30

Lys Leu Leu Ile Gln Ala Glu Phe Pro Cys Leu Leu Lys Gly Pro Asn
            35                  40                  45

Thr Leu Asp Asp Leu Phe Gln Glu Leu Asp Lys Asn Gly
    50                  55                  60

<210> SEQ ID NO 4
<211> LENGTH: 61
<212> TYPE: PRT
<213> ORGANISM: Artificial sequence
<220> FEATURE:
<223> OTHER INFORMATION: Synthetic peptide

<400> SEQUENCE: 4

Met Ser Thr Lys Lys Ser Pro Cys Glu Leu Lys Arg Ile Phe Glu Lys
1               5                   10                  15

Tyr Ala Ala Lys Glu Gly Asp Pro Asp Gln Leu Ser Lys Asp Glu Leu
                20                  25                  30

Lys Leu Leu Ile Gln Ala Glu Phe Pro Ser Leu Leu Lys Gly Pro Asn
            35                  40                  45

Thr Leu Asp Asp Leu Phe Gln Glu Leu Asp Lys Asn Gly
    50                  55                  60

<210> SEQ ID NO 5
<211> LENGTH: 52
<212> TYPE: DNA
<213> ORGANISM: Artificial sequence
<220> FEATURE:
<223> OTHER INFORMATION: forward primer

<400> SEQUENCE: 5
cttgttcgtg gtcgtggtgg atccggagga gcatttgaga tcttagcaaa tg          52

<210> SEQ ID NO 6
<211> LENGTH: 52
<212> TYPE: DNA
<213> ORGANISM: Artificial sequence
<220> FEATURE:
```

<223> OTHER INFORMATION: reverse primer

<400> SEQUENCE: 6
gaacgtgcct tctgcgtgtc cggaacccga tttcaaaaaa ggcttcatct tc    52

<210> SEQ ID NO 7
<211> LENGTH: 52
<212> TYPE: DNA
<213> ORGANISM: Artificial sequence
<220> FEATURE:
<223> OTHER INFORMATION: forward primer

<400> SEQUENCE: 7
ggccaagccg ccagggaatt cattgcatgg cttgttcgtg gtcgtggtgg at    52

<210> SEQ ID NO 8
<211> LENGTH: 48
<212> TYPE: DNA
<213> ORGANISM: Artificial sequence
<220> FEATURE:
<223> OTHER INFORMATION: reverse primer

<400> SEQUENCE: 8
ttcgaggtag ctgcttacgt cgctcgtgaa cgtgccttct gcgtgtcc    48

<210> SEQ ID NO 9
<211> LENGTH: 28
<212> TYPE: DNA
<213> ORGANISM: Artificial sequence
<220> FEATURE:
<223> OTHER INFORMATION: serine 42 forward primer

<400> SEQUENCE: 9
tgtttactca aaggtccaaa caccctag    28

<210> SEQ ID NO 10
<211> LENGTH: 24
<212> TYPE: DNA
<213> ORGANISM: Artificial sequence
<220> FEATURE:
<223> OTHER INFORMATION: serine 42 reverse primer

<400> SEQUENCE: 10
ggggaattca gcctgaatca atag    24

<210> SEQ ID NO 11
<211> LENGTH: 31
<212> TYPE: DNA
<213> ORGANISM: Artificial sequence
<220> FEATURE:
<223> OTHER INFORMATION: glutamate8 forward primer

<400> SEQUENCE: 11
tgtgaactga agaggatttt tgaaaaatat g    31

<210> SEQ ID NO 12
<211> LENGTH: 24
<212> TYPE: DNA
<213> ORGANISM: Artificial sequence
<220> FEATURE:
<223> OTHER INFORMATION: glutamate8 forward primer

<400> SEQUENCE: 12
aggagacttt ttagtactca tatg    24

<210> SEQ ID NO 13

```
<211> LENGTH: 79
<212> TYPE: PRT
<213> ORGANISM: Artificial sequence
<220> FEATURE:
<223> OTHER INFORMATION: human calbindin D9K

<400> SEQUENCE: 13

Met Ser Thr Lys Lys Ser Pro Glu Glu Leu Lys Arg Ile Phe Glu Lys
1               5                   10                  15

Tyr Ala Ala Lys Glu Gly Asp Pro Asp Gln Leu Ser Lys Asp Glu Leu
            20                  25                  30

Lys Leu Leu Ile Gln Ala Glu Phe Pro Ser Leu Leu Lys Gly Pro Asn
        35                  40                  45

Thr Leu Asp Asp Leu Phe Gln Glu Leu Asp Lys Asn Gly Asp Gly Glu
    50                  55                  60

Val Ser Phe Glu Glu Phe Gln Val Leu Val Lys Ile Ser Gln
65                  70                  75

<210> SEQ ID NO 14
<211> LENGTH: 92
<212> TYPE: PRT
<213> ORGANISM: Artificial sequence
<220> FEATURE:
<223> OTHER INFORMATION: Fusion protein Cal.GLP

<400> SEQUENCE: 14

Met Ser Thr Lys Lys Ser Pro Glu Glu Leu Lys Arg Ile Phe Glu Lys
1               5                   10                  15

Tyr Ala Ala Lys Glu Gly Asp Pro Asp Gln Leu Ser Lys Asp Glu Leu
            20                  25                  30

Lys Leu Leu Ile Gln Ala Glu Phe Pro Ser Leu Leu Lys Gly Pro Asn
        35                  40                  45

Thr Leu Asp Asp Leu Phe Gln Glu Leu Asp Lys Asn Gly His Ala Glu
    50                  55                  60

Gly Thr Phe Thr Ser Asp Val Ser Ser Tyr Leu Glu Gly Gln Ala Ala
65                  70                  75                  80

Lys Glu Phe Ile Ala Trp Leu Val Lys Gly Arg Gly
            85                  90

<210> SEQ ID NO 15
<211> LENGTH: 92
<212> TYPE: PRT
<213> ORGANISM: Artificial sequence
<220> FEATURE:
<223> OTHER INFORMATION: serine 42 variant

<400> SEQUENCE: 15

Met Ser Thr Lys Lys Ser Pro Glu Glu Leu Lys Arg Ile Phe Glu Lys
1               5                   10                  15

Tyr Ala Ala Lys Glu Gly Asp Pro Asp Gln Leu Ser Lys Asp Glu Leu
            20                  25                  30

Lys Leu Leu Ile Gln Ala Glu Phe Pro Cys Leu Leu Lys Gly Pro Asn
        35                  40                  45

Thr Leu Asp Asp Leu Phe Gln Glu Leu Asp Lys Asn Gly His Ala Glu
    50                  55                  60

Gly Thr Phe Thr Ser Asp Val Ser Ser Tyr Leu Glu Gly Gln Ala Ala
65                  70                  75                  80

Lys Glu Phe Ile Ala Trp Leu Val Lys Gly Arg Gly
            85                  90
```

-continued

```
<210> SEQ ID NO 16
<211> LENGTH: 92
<212> TYPE: PRT
<213> ORGANISM: Artificial sequence
<220> FEATURE:
<223> OTHER INFORMATION: glutamate8 variant

<400> SEQUENCE: 16

Met Ser Thr Lys Lys Ser Pro Cys Glu Leu Lys Arg Ile Phe Glu Lys
1               5                   10                  15

Tyr Ala Ala Lys Glu Gly Asp Pro Asp Gln Leu Ser Lys Asp Glu Leu
            20                  25                  30

Lys Leu Leu Ile Gln Ala Glu Phe Pro Ser Leu Lys Gly Pro Asn
        35                  40                  45

Thr Leu Asp Asp Leu Phe Gln Glu Leu Asp Lys Asn Gly His Ala Glu
50                  55                  60

Gly Thr Phe Thr Ser Asp Val Ser Ser Tyr Leu Glu Gly Gln Ala Ala
65                  70                  75                  80

Lys Glu Phe Ile Ala Trp Leu Val Lys Gly Arg Gly
            85                  90

<210> SEQ ID NO 17
<211> LENGTH: 61
<212> TYPE: PRT
<213> ORGANISM: Artificial Sequence
<220> FEATURE:
<223> OTHER INFORMATION: Synthetic peptide

<400> SEQUENCE: 17

Met Ser Thr Lys Lys Ser Pro Glu Glu Leu Lys Arg Ile Phe Glu Lys
1               5                   10                  15

Tyr Ala Ala Lys Glu Gly Asp Pro Asp Asp Leu Ser Lys Asp Glu Leu
            20                  25                  30

Lys Leu Leu Ile Gln Ala Glu Phe Pro Cys Leu Leu Lys Gly Pro Asn
        35                  40                  45

Thr Leu Asp Asp Leu Phe Gln Glu Leu Asp Lys Asn Gly
50                  55                  60

<210> SEQ ID NO 18
<211> LENGTH: 91
<212> TYPE: PRT
<213> ORGANISM: Artificial Sequence
<220> FEATURE:
<223> OTHER INFORMATION: Synthetic Peptide

<400> SEQUENCE: 18

Met Ser Thr Lys Lys Ser Pro Glu Glu Leu Lys Arg Ile Phe Glu Lys
1               5                   10                  15

Tyr Ala Ala Lys Glu Gly Asp Pro Asp Asp Leu Ser Lys Asp Glu Leu
            20                  25                  30

Lys Leu Leu Ile Gln Ala Glu Phe Pro Cys Leu Leu Lys Gly Pro Asn
        35                  40                  45

Thr Leu Asp Asp Leu Phe Gln Glu Leu Asp Lys Asn Gly His Ala Glu
50                  55                  60

Gly Thr Phe Thr Ser Asp Val Ser Ser Tyr Leu Glu Gly Gln Ala Ala
65                  70                  75                  80

Lys Glu Phe Ile Ala Trp Leu Val Lys Gly Arg
            85                  90
```